(12) United States Patent
Mistretta

(10) Patent No.: US 7,519,412 B2
(45) Date of Patent: Apr. 14, 2009

(54) HIGHLY CONSTRAINED IMAGE RECONSTRUCTION METHOD

(75) Inventor: Charles A. Mistretta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/482,372

(22) Filed: Jul. 7, 2006

(65) Prior Publication Data

US 2007/0010731 A1    Jan. 11, 2007

Related U.S. Application Data

(60) Provisional application No. 60/697,607, filed on Jul. 8, 2005, provisional application No. 60/719,445, filed on Sep. 22, 2005.

(51) Int. Cl.
- *A61B 5/05* (2006.01)
- *G01V 3/00* (2006.01)
- *G01T 1/166* (2006.01)

(52) U.S. Cl. ............... 600/407; 324/307; 600/410; 600/425; 250/363.04

(58) Field of Classification Search .......... 600/407, 600/410; 324/314; 378/4; 382/128–133, 382/294

See application file for complete search history.

(56) References Cited

U.S. PATENT DOCUMENTS

| | | | |
|---|---|---|---|
| 5,502,385 A | 3/1996 | Kuhn et al. | |
| 5,603,322 A | 2/1997 | Jesmanowicz et al. | |
| 5,604,778 A | 2/1997 | Polacin et al. | |
| 5,933,006 A | 8/1999 | Rasche et al. | |
| 6,324,245 B1 * | 11/2001 | Tam .................... | 378/4 |
| 6,487,435 B2 | 11/2002 | Mistretta et al. | |
| 6,490,472 B1 | 12/2002 | Li et al. | |
| 6,710,686 B2 | 3/2004 | Mertelmeier et al. | |
| 6,807,248 B2 | 10/2004 | Mihara et al. | |
| 6,954,067 B2 | 10/2005 | Mistretta | |
| 2001/0027262 A1 | 10/2001 | Mistretta et al. | |

FOREIGN PATENT DOCUMENTS

| | | |
|---|---|---|
| EP | 0 627 633 A1 | 12/1994 |
| WO | WO 2005/026765 | 3/2005 |
| WO | WO 2005/069031 | 7/2005 |

OTHER PUBLICATIONS

Liang and Lauterbur, Constrained Imaging, IEEE Engineering in Medicine and Biology, 1996.

(Continued)

*Primary Examiner*—Eric F Winakur
*Assistant Examiner*—Michael T Rozanski
(74) *Attorney, Agent, or Firm*—Quarles & Brady LLP

(57) ABSTRACT

An image reconstruction method includes reconstructing a composite image of a subject using a conventional reconstruction method. The composite image employs the best information available regarding the subject of the scan and this information is used to constrain the reconstruction of highly undersampled image frames. An image frame is reconstructed using limited acquired data and image quality is improved using a priori information of the subject by weighting pixel values therein by values of corresponding pixels in the composite image.

43 Claims, 21 Drawing Sheets

OTHER PUBLICATIONS

Liang, Madori, Glover and Pelc, "Fast Algorithms of GS-Model-Based Image Reconstruction in Data-Sharing Fourier Imaging," IEEE Transactions, 22;8:2003.

Pruessmann, Weiger, Bornert & Boesiger, "Advances In Sensitivity Encoding With Arbitrary k-Space Trajectories", Mag. Reson. Med. 46:638-651 (2001).

Wieslaw L. Nowinski, The Iterated Normalized Backprojection Method of Image Reconstruction, Institute of Computer Science, Polish Academy of Sciences Ordona 21, 01-237 Warsaw, Poland.

Y. Huang et al, Time-Resolved 3D MR Angiography by Interleaved Biplane Projection, Proc. Intl. Soc. Mag. Reson. Med. 13 (2005).

T.A. Cashen et al, Comparison of Temporal and Spatial Undersampling Techniques for Time-Resolved Contrast-Enhanced MR Angiography, Proc. Intl. Soc. Mag. Reson. Med. 13, (2005).

Graeme C. McKinnon et al, Towards Imaging the Beating Heart Usefully with a Conventional CT Scanner, Trans. on Biomedical Eng., vol. BME-28, No. 2, p. 123-127, Feb. 1981.

Kathryn L. Garden et al, 3-D Reconstruction of the Heart from few Projections: A Practical Implementation of the McKinnon-Bates Algorithm, Trans. on Biomedical Eng., vol. MI-5, No. 4, p. 233-234, Dec. 1986.

A.L. Wentland et al, Technique for Acquiring MR Images of CSF Flow During a Valsalva Maneuver, Med. Phys. Univ. of WI, Madison WI.

K.M. Johnson et al, Average and Time-Resolved Dual Velocity Encoded Phase Contrast Vastly Undersampled Isotropic Projection Imaging, Med. Phys. Univ. of WI, Madison WI.

K.M. Johnson et al, Transtenotic Pressure Gradient Measurements Using Phase Contrast Vastly Undersampled Isotropic Projection Imaging (PC-VIPR) in a Canin Model, Med. Phys. Univ. of WI, Madison WI.

C.A. Mistretta et al, Highly Constrained Backprojection for Time-Resolved MRI, Mag. Reson. Med. 55:30-40 (2006).

Zhi-Pei Liang et al, Constrained Reconstruction Methods in MR Imaging, Reviews of Mag. Reson. in Med. vol. 4, pp. 67-185, 1992.

J.G. Pipe et al, Spiral Projection Imaging: a new fast 3D trajectory, Proc. Intl. Soc. Mag. Reson. Med. 13, (2005).

K.V. Koladia et al, Rapid 3D PC-MRA using Spiral Projection Imaging, Proc. Intl. Soc. Mag. Reson. Med. 13, (2005).

J. Tsao et al, k-t Blast and k-t Sense: Dynamic MRI With High Frame Rate Exploiting Spatiotemporal Correlations, Mag. Reson. Med. 50:1031-1042 (2003).

Zhi-Pei Liang et al, Constrained Imaging—Overcoming the Limitations of the Fourier Series, IEEE Engineering in Medicine and Biology, Sep./Oct. 1996, pp. 126-132.

Zhi-Pei Liang et al, Fast Algorithm for GS-Model-Based Image Reconstruction in Data-Sharing Fourier Imaging, IEEE Transactions on Med. Imaging, vol. 22, No. 8, pp. 1026-1030, Aug. 2003.

Klass P. Pruessmann et al, Advances in Sensitivity Encoding With Arbitrary k-Space Trajectories, Mag. Reson. in Med. 46:638-651 (2001).

R. Fahrig et al, Use of a C-Arm System to Generate True Three-dimensional Computed Rotational Angiograms: Preliminary In Vitro and In Vivo Results, AJNR: 18, pp. 1507-1514, Sep. 1997.

A.V. Barger, et al, Single Breath-Hold 3D Contrast-Enhanced Method for Assessment of Cardiac Function, Mag. Reson. in Med. 44:821-824 (2000).

J. Du et al, Time-Resolved Undersampled Projection Reconstruction Imaging for High-Resolution CE-MRA of the Distal Runoff Vessels, Mag. Reson. in Med. 48:516-522 (2002).

Ashwani Aggarwal et al, Imaging In Turbid Media by Modified Filtered Back Projection Method Using Data From Monte Carlo Simulation, Proc. of SPIE vol. 5047, pp. 314-324.

Xavier Golay, et al, Presto-Sense: An Ultrafast Whole-Brain fMRI Technique, Mag. Reson. in Med. 43:779-786 (2000).

Ronald R. Price, et al, Practical Aspects of Functional MRI (NMR Task Group #6), Medical Physics, vol. 29, No. 8, pp. 1892-1912, Aug. 2002.

M.S. Hansen et al, k-t Blast Reconstruction From Arbitrary k-t space Sampling: Application To Dynamic Radial Imaging, Proc. Intl. Soc. Mag. Reson. Med. 13 p. 684 (2005).

P. Schmidlin et al; Subsets and Overrelaxation In Iterative Image Reconstruction; Phys. Med. Biol. 44 (1999) 1385-1396.

L. Launay et al; 3D Reconstruction Of Cerebral Vessels and Pathologies From A Few Biplane Digital Angiographies; pp. 123-128.

C. Badea et al; Experiments With The Nonlinear And Chaotic Behavior of the Multiplicative Algebraic Reconstruction Technique (MART) Algorithm for Computed Tomography; Phys. Med. Biol. 49 (2004) 1455-1474.

R. Boubertakh et al., Dynamic Images Reconstruction using kt-Blast without Training Data, Proc. Intl. Soc. Med. 11 p. 343 (2004).

P. Irarrazaval et al., Reconstruction of Undersampled Dynamic Images Based on Time Frame Registration, Proc. Intl. Soc. Med. 11 p. 342 (2004).

J. Tsao et al., Optimized canonical sampling patterns in k-t space with two and three spatial dimensions for k-t Blast and k-t', Proc. Intl. Soc. Med. 11 p. 261 (2004).

M.S. Hansen et al., A study of the spatial-temporal tradeoff in k-t Blast reconstruction, Proc. Intl. Soc. Med. 11 p. 536 (2004).

J. Tsao et al., Moving-buffer k-t Blast for real-time reconstruction: Cartesian & simplified radial cases, Proc. Intl. Soc. Med. 11 p. 635 (2004).

F. Huang et al., Reconstruction with Prior Information for Dynamic MRI, Proc. Intl. Soc. Med. 11 p. 2680 (2004).

D. Mitsouras et al., Accelerated MR Imaging via FOLDing the non-Fourier Encoded Dimensions, Proc. Intl. Soc. Med. 11 p. 2092 (2004).

P.C. Lauterbur and Z. Liang, Magnetic Resonance Imaging with a priori Constraints: Possibilities and Limitations, IEEE Engineering in Medicine and Biology Society, 1996.

C. Baltes et al., Considerations on training data in k-t Blast / k-t Sense accelerated quantitative flow measurements, Proc. Intl. Soc. Mag. Reson. Med. 13 p. 383 (2005).

M.S. Hansen et al., On the Influence of Training Data Quality in k-t Blast Reconstruction, Mag. Reson. Med. 52:1175-1183 (2004).

M. Lustig et al., k-t Sparse: High Frame Rate Dynamic MRI Exploiting Spatio-Temporal Sparsity, Proc. Intl. Soc. Mag. Reson. Med. 14 (2006).

J. Tsao et al., Unifying Linear Prior-Information-Driven Methods for Accelerated Image Acquisition, Mag. Reson. Med. 46:652-660 (2001).

Q. Xiang and R.M. Henkelman, K-Space Description for MR Imaing of Dynamic Objects, Mag. Reson. Med. 29:422-428 (1993).

M. Lustig et al., Rapid MR Imaging with Compressed Sensing and Randomly Under-Sampled 3DFT Trajectories, Proc. Intl. Soc. Mag. Reson. Med. 14 (2006).

S. Krishnan and T.L. Chenevert, Spatio-Temporal Bandwidth-Based Acquisition for Dynamic Contrast-Enhanced Magnetic Resonance Imaging, J. Mag. Reson. Imaging 20:129-137 (2004).

M.S. Hansen et al., k-t Blast Reconstruction From Non-Cartesian k-t Space Sampling, Mag. Reson. Med. 55:85-91 (2006).

A.G. Webb et al., Application of Reduced-Encoding MR Imaging with Generalized-Series Reconstruction (RIGR), J. Mag. Reson. Imaging 3:925-928 (1993), B. Madore and N.J. Pelc, New Approach to 3D Time-Resolved Angiography, Mag. Reson. Med. 47:1022-1025 (2002).

J. Tsao et al., Optimizing Spatiotemporal Sampling for k-t Blast and k-t Sense: Application to High-Resolution Real-Time Cardiac Steady-State Free Precession, Mag. Reson. Med. 53:1372-1382 (2005).

* cited by examiner

HIGHLY CONSTRAINED IMAGE RECONSTRUCTION METHOD

CROSS-REFERENCE TO RELATED APPLICATIONS

This application is based on U.S. Provisional Patent Application Ser. No. 60/697,607 filed on Jul. 8, 2005 and entitled "BACKPROJECTION RECONSTRUCTION METHOD FOR UNDERSAMPLED TIME-RESOLVED MR IMAGING" and on U.S. Provisional Patent Application Ser. No. 60/719,445 filed on Sep. 22, 2005 and entitled "HIGHLY CONSTRAINED IMAGE RECONSTRUCTION METHOD."

STATEMENT REGARDING FEDERALLY SPONSORED RESEARCH

This invention was made with government support under Grant Nos. HL066488 and HL072260 awarded by the National Institute of Health. The United States Government has certain rights in this invention.

BACKGROUND OF THE INVENTION

The field of the invention is medical imaging and particularly, methods for reconstructing images from acquired image data.

Magnetic resonance imaging (MRI) uses the nuclear magnetic resonance (NMR) phenomenon to produce images. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins, and after the excitation signal $B_1$ is terminated, this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. Each measurement is referred to in the art as a "view" and the number of views determines the quality of the image. The resulting set of received NMR signals, or views, or k-space samples, are digitized and processed to reconstruct the image using one of many well known reconstruction techniques. The total scan time is determined in part by the length of each measurement cycle, or "pulse sequence", and in part by the number of measurement cycles, or views, that are acquired for an image. There are many clinical applications where total scan time for an image of prescribed resolution and SNR is a premium, and as a result, many improvements have been made with this objective in mind.

Projection reconstruction methods have been known since the inception of magnetic resonance imaging and this method is again being used as disclosed in U.S. Pat. No. 6,487,435. Rather than sampling k-space in a rectilinear, or Cartesian, scan pattern as is done in Fourier imaging and shown in FIG. 2A, projection reconstruction methods sample k-space with a series of views that sample radial lines extending outward from the center of k-space as shown in FIG. 2B. The number of views needed to sample k-space determines the length of the scan and if an insufficient number of views are acquired, streak artifacts are produced in the reconstructed image. The technique disclosed in U.S. Pat. No. 6,487,435 reduces such streaking by acquiring successive undersampled images with interleaved views and sharing peripheral k-space data between successive image frames.

In a computed tomography ("CT") system, an x-ray source projects a fan-shaped beam which is collimated to lie within an X-Y plane of a Cartesian coordinate system, termed the "image plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce what is called the "transmission profile".

The source and detector array in a conventional CT system are rotated on a gantry within the imaging plane and around the object so that the angle at which the x-ray beam intersects the object constantly changes. The transmission profile from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object.

As with MRI, there are a number of clinical applications for x-ray CT where scan time is at a premium. In time-resolved angiography, for example, a series of image frames are acquired as contrast agent flows into the region of interest. Each image is acquired as rapidly as possible to obtain a snapshot that depicts the inflow of contrast. This clinical application is particularly challenging when imaging coronary arteries or other vessels that require cardiac gating to suppress motion artifacts.

There are two methods used to reconstruct images from an acquired set of projection views as described, for example, in U.S. Pat. No. 6,710,686. In MRI the most common method is to regrid the k-space samples from their locations on the radial sampling trajectories to a Cartesian grid. The image is then reconstructed by performing a 2D or 3D Fourier transformation of the regridded k-space samples. The second method for reconstructing an MR image is to transform the radial k-space projection views to Radon space by first Fourier transforming each projection view. An image is reconstructed from these signal projections by filtering and back-projecting them into the field of view (FOV). As is well known in the art, if the acquired signal projections are insufficient in number to satisfy the Nyquist sampling theorem, streak artifacts are produced in the reconstructed image.

The prevailing method for reconstructing an image from 2D x-ray CT data is referred to in the art as the filtered backprojection technique. This backprojection process is essentially the same as that used in MR image reconstruction discussed above and it converts the attenuation signal measurements acquired in the scan into integers called "CT numbers" or "Hounsfield units", which are used to control the brightness of a corresponding pixel on a display.

The standard backprojection method used in both the MRI and x-ray CT is graphically illustrated in FIG. 3. Each acquired signal projection profile 10 is backprojected onto the field of view 12 by projecting each signal sample 14 in the profile 10 through the FOV 12 along the projection path as indicted by arrows 16. In backprojecting each signal sample 14 into the FOV 12 no a priori knowledge of the subject being imaged is used and the assumption is made that the signals in the FOV 12 are homogeneous and that the signal sample 14 should be distributed equally in each pixel through which the projection path passes. For example, a projection path 8 is illustrated in FIG. 3 for a single signal sample 14 in one signal projection profile 10 as it passes through N pixels in the FOV 12. The signal value (P) of this signal sample 14 is divided up equally between these N pixels:

$$S_n = (P \times 1)/N \qquad (1)$$

where: $S_n$ is the signal value distributed to the $n^{th}$ pixel in a projection path having N pixels.

Clearly, the assumption that the backprojected signal in the FOV 12 is homogeneous is not correct. However, as is well known in the art, if certain corrections are made to each signal profile 10 and a sufficient number of profiles are acquired at a corresponding number of projection angles, the errors caused by this faulty assumption are minimized and image artifacts are suppressed. In a typical, filtered backprojection method of image reconstruction, 400 projections are required for a 256×256 pixel 2D image and 203,000 projections are required for a 256×256×256 voxel 3D image.

SUMMARY OF THE INVENTION

The present invention is a new method for reconstructing medical images, and particularly, an improved method for reconstructing an image from projection views of the subject. A composite image is reconstructed from acquired data to provide a priori knowledge of the subject being imaged. This composite image is then used to highly constrain the image reconstruction process. The invention may be used in a number of different imaging modalities including magnetic resonance imaging (MRI), x-ray computed tomography (CT), positron emission tomography (PET), single photon emission computed tomography (SPECT) and digital tomosynthesis (DTS).

A discovery of the present invention is that good quality images can be produced with far fewer projection signal profiles if a priori knowledge of the signal contour in the FOV 12 is used in the reconstruction process. Referring to FIG. 4, for example, the signal contour in the FOV 12 may be known to include structures such as blood vessels 18 and 20. That being the case, when the backprojection path 8 passes through these structures a more accurate distribution of the signal sample 14 in each pixel is achieved by weighting the distribution as a function of the known signal contour at that pixel location. As a result, a majority of the signal sample 14 will be distributed in the example of FIG. 4 at the backprojection pixels that intersect the structures 18 and 20. For a backprojection path 8 having N pixels this highly constrained backprojection may be expressed as follows:

$$S_n = (P \times C_n) \bigg/ \sum_{n=1}^{N} C_n \qquad (2)$$

where: $S_n$=the backprojected signal magnitude at a pixel n in an image frame being reconstructed;
P=the signal sample value in the projection profile being backprojected; and
$C_n$=signal value of an a priori composite image at the $n^{th}$ pixel along the backprojection path. The composite image is reconstructed from data acquired during the scan, and may include that used to reconstruct the image frame as well as other acquired image data that depicts the structure in the field of view. The numerator in equation (2) weights each pixel using the corresponding signal value in the composite image and the denominator normalizes the value so that all backprojected signal samples reflect the projection sums for the image frame and are not multiplied by the sum of the composite image.

It should be noted that while the normalization can be performed on each pixel separately after the backprojection, in many clinical applications it is far easier to normalize the projection P before the backprojection. In this case, the projection P is normalized by dividing by the corresponding value $P_c$ in a projection through the composite image at the same view angle. The normalized projection $P/P_c$ is then backprojected and the resulting image is then multiplied by the composite image.

A 3D embodiment of the highly constrained backprojection is shown pictorially in FIG. 5 for a single 3D projection view characterized by the view angles θ and φ. This projection view is back projected along axis 16 and spread into a Radon plane 21 at a distance r along the back projection axis 16. Instead of a filtered back projection in which projection signal values are filtered and uniformly distributed into the successive Radon planes, along axis 16, the projection signal values are distributed in the Radon plane 21 using the information in the composite image. The composite image in the example of FIG. 5 contains vessels 18 and 20. The weighted signal contour value is deposited at image location x, y, z in the Radon plane 21 based on the intensity at the corresponding location x, y, z in the composite image. This is a simple multiplication of the backprojected signal profile value P by the corresponding composite image voxel value. This product is then normalized by dividing the product by the projection profile value from the corresponding image space projection profile formed from the composite image. The formula for the 3D reconstruction is $$I(x, y, z) = \sum (P(r, \theta, \phi) * C(x, y, z)_{(r,\theta,\phi)} / P_c(r, \theta, \phi)) \qquad (2a)$$

where the sum (Σ) is over all projections in the image frame being reconstructed and the x, y, z values in a particular Radon plane are calculated using the projection profile value $P(r,\theta,\phi)$ at the appropriate r,θ,φ value for that plane. $P_c(r,\theta,\phi)$ is the corresponding projection profile value from the composite image, and $C(x,y,z)_{r,\theta,\phi}$ is the composite image value at (r,θ,φ).

Another discovery of the present invention is that there are a number of clinical applications in which a priori information is acquired during a scan and a composite image can be reconstructed and used to constrain the reconstruction of undersampled or low dose image frames. As shown in FIG. 1, when a series of time-resolved images 2 are acquired in a dynamic study, for example, each image frame 2 may be reconstructed using a very limited set of acquired views. However, each such set of views is interleaved with the views acquired for other image frames 2, and after a number of image frames have been acquired, a sufficient number of different views are available to reconstruct a quality composite image 3 for use according to the present invention. This is illustrated in FIG. 6, where dotted lines 30 indicate projection views acquired in one image frame, dashed lines 32 indicate interleaved projection views acquired in a second image frame, and lines 34 indicate interleaved projection views acquired in a third image frame. Whereas the sampling density necessary to meet the Nyquist criteria may extend only a short radial distance (r) for any one image frame, by combining the interleaved projection profiles of all three image frames this distance is extended to the much larger radius R. A composite image 3 formed by using all the interleaved projections is thus much higher quality, and this higher quality is conveyed to the image frame by using the highly constrained image reconstruction method 4 of the present invention. The image frames 2 may also be acquired in a dynamic study in which the dosage (e.g., x-ray) or exposure time (e.g., PET or SPECT) is reduced for each image frame. In this case the composite image is formed by accumulating or averaging measurements from the series of acquired image frames. The highly constrained reconstruction 4 of each image frame 2 conveys the higher SNR of this composite image to the resulting reconstructed image.

While the present invention is best understood as a highly constrained backprojection of each projection view into the FOV 12, other less intuitive methods are mathematically equivalent. For example, rather than multiplying backprojected signal profile samples P by corresponding normalized composite image pixel values C as set forth above in equation (2) and then summing the results for each backprojected profile, all of the signal profiles can be normalized and backprojected (in an unfiltered and unconstrained manner) and summed to form an image data set. This artifact ridden image is then multiplied by corresponding pixel values in the composite image to form a constrained image. Normalization in this case requires that projections $P_c$ of the composite image C be calculated at each projection profile angle as shown in FIG. 7. That is, for every projection profile used to reconstruct this particular image frame, a composite image projection $P_c$ is calculated at the same view angle. Then, as shown in FIG. 8, the projection profiles are normalized by dividing each by the composite image projection values $P_c$ located in the same ray path. For example, the backprojected pixels located in ray path 36 are each divided by a composite image projection value 38 that lies in the same ray path, and the backprojected image pixels located in ray path 40 are divided by composite image projection value 42 that lies in the same ray path. In short, each backprojected image pixel lies in the ray path with at least one composite image projection value in each composite image projection $P_c$ and normalization is achieved by dividing by all these values.

In addition, the present invention may be practiced as a modification to a Fast Fourier Transformation (FFT) image reconstruction process. For example, the composite image may be produced by combining all the acquired projection views in k-space, regridding the k-space samples to a Cartesian coordinate system, and then performing an inverse 2D or 3D Fourier transformation. Each acquired frame image view is normalized in Radon space, transformed to k-space, combined with the other normalized k-space views and used to reconstruct an unconstrained frame image in the same manner using a 2DFT or 3DFT. The unconstrained frame image is then multiplied by the composite image. Normalization of each frame image view may also be performed in k-space rather than Radon space although it is a more complex operation. Whereas normalization in Radon space is a multiplication ($1/P_c$) operation, the same step in k-space is a convolution operation.

A general object of the invention is to improve the reconstruction of medical images by constraining the reconstruction process with a priori information regarding the subject of the image. The improvement resulting from the present invention can manifest itself in a number of ways, including reduction of scan time, reduction in radiation dose and higher time resolution in time resolved studies.

Another object of the invention is to improve the signal-to-noise ratio (SNR) of a highly undersampled image. It has been discovered that the higher SNR of a more highly sampled composite image is imparted to the highly under sampled image when it is reconstructed according to the present invention.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

The present invention may be applied to many different medical imaging modalities and to many different clinical applications. A number of these clinical applications of the invention are described below to illustrate the broad scope of the present invention.

Figure 9:
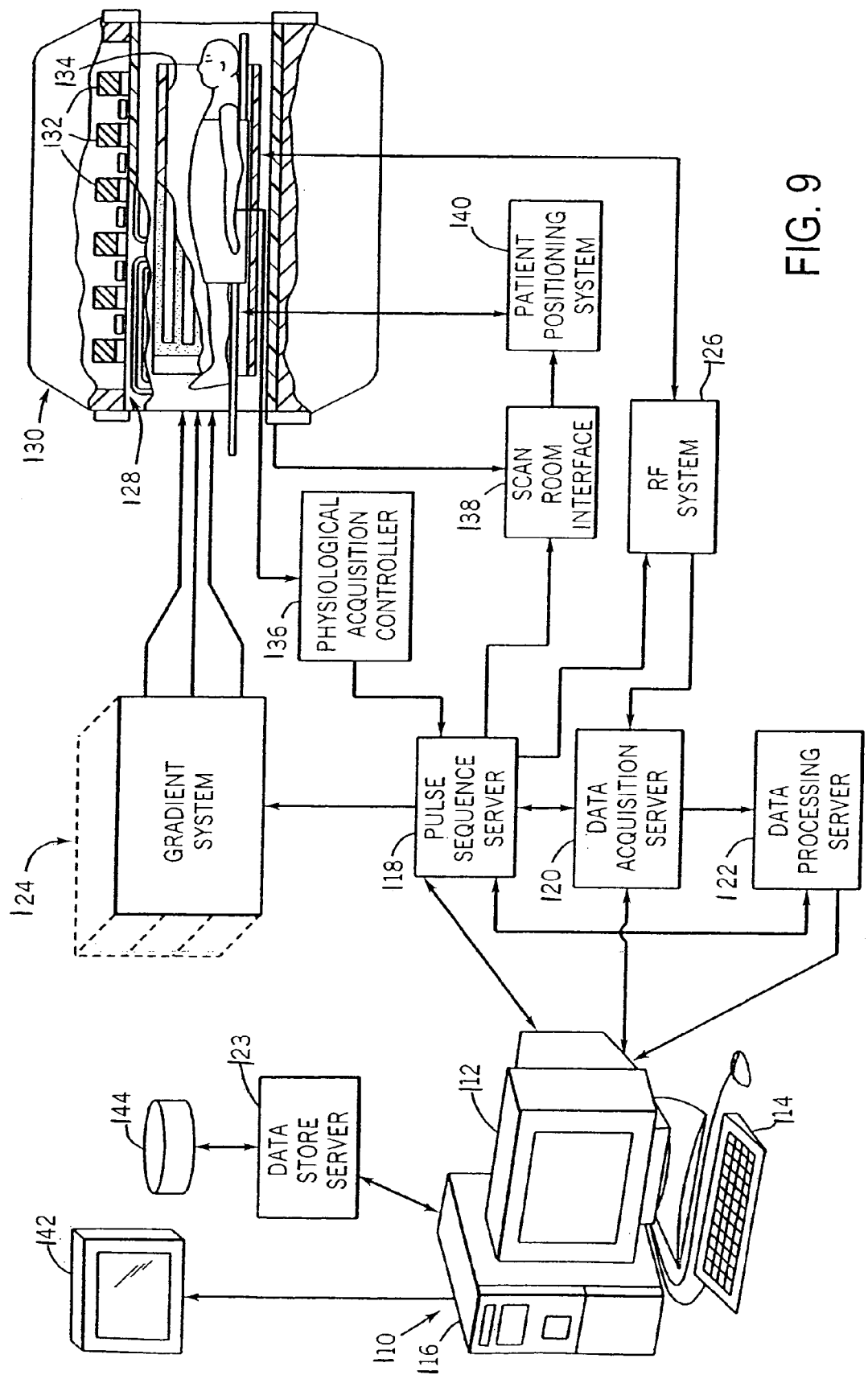
FIG. 9 is a block diagram of a magnetic resonance imaging (MRI) system used to practice the present invention.

Referring particularly to FIG. 9, a preferred embodiment of the invention is employed in an MRI system. The MRI system includes a workstation 110 having a display 112 and a keyboard 114. The workstation 110 includes a processor 116 which is a commercially available programmable machine running a commercially available operating system. The workstation 110 provides the operator interface which enables scan prescriptions to be entered into the MRI system.

The workstation 110 is coupled to four servers: a pulse sequence server 118; a data acquisition server 120; a data processing server 122, and a data store server 23. In the preferred embodiment the data store server 123 is performed by the workstation processor 116 and associated disc drive interface circuitry. The remaining three servers 118, 120 and 122 are performed by separate processors mounted in a single enclosure and interconnected using a 64-bit backplane bus. The pulse sequence server 118 employs a commercially available microprocessor and a commercially available quad communication controller. The data acquisition server 120 and data processing server 122 both employ the same commercially available microprocessor and the data processing server 122 further includes one or more array processors based on commercially available parallel vector processors.

The workstation 110 and each processor for the servers 18, 20 and 22 are connected to a serial communications network. This serial network conveys data that is downloaded to the servers 118, 120 and 122 from the workstation 110 and it conveys tag data that is communicated between the servers and between the workstation and the servers. In addition, a high speed data link is provided between the data processing server 122 and the workstation 110 in order to convey image data to the data store server 123.

The pulse sequence server 118 functions in response to program elements downloaded from the workstation 110 to operate a gradient system 124 and an RF system 126. Gradient waveforms necessary to perform the prescribed scan are produced and applied to the gradient system 124 which excites gradient coils in an assembly 128 to produce the magnetic field gradients $G_x$, $G_y$ and $G_z$ used for position encoding NMR signals. The gradient coil assembly 128 forms part of a magnet assembly 130 which includes a polarizing magnet 132 and a whole-body RF coil 134.

RF excitation waveforms are applied to the RF coil 134 by the RF system 126 to perform the prescribed magnetic resonance pulse sequence. Responsive NMR signals detected by the RF coil 134 are received by the RF system 126, amplified, demodulated, filtered and digitized under direction of commands produced by the pulse sequence server 118. The RF system 126 includes an RF transmitter for producing a wide variety of RF pulses used in MR pulse sequences. The RF transmitter is responsive to the scan prescription and direction from the pulse sequence server 118 to produce RF pulses of the desired frequency, phase and pulse amplitude waveform. The generated RF pulses may be applied to the whole body RF coil 134 or to one or more local coils or coil arrays.

The RF system 126 also includes one or more RF receiver channels. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2+Q^2}$$

and the phase of the received NMR signal may also be determined:

$$\phi=\tan^{-1} Q/I.$$

The pulse sequence server 118 also optionally receives patient data from a physiological acquisition controller 136. The controller 136 receives signals from a number of different sensors connected to the patient, such as ECG signals from electrodes or respiratory signals from a bellows. Such signals are typically used by the pulse sequence server 118 to synchronize, or "gate", the performance of the scan with the subject's respiration or heart beat.

The pulse sequence server 118 also connects to a scan room interface circuit 138 which receives signals from various sensors associated with the condition of the patient and the magnet system. It is also through the scan room interface circuit 138 that a patient positioning system 140 receives commands to move the patient to desired positions during the scan.

It should be apparent that the pulse sequence server 118 performs real-time control of MRI system elements during a scan. As a result, it is necessary that its hardware elements be operated with program instructions that are executed in a timely manner by run-time programs. The description components for a scan prescription are downloaded from the workstation 110 in the form of objects. The pulse sequence server 118 contains programs which receive these objects and converts them to objects that are employed by the run-time programs.

The digitized NMR signal samples produced by the RF system 126 are received by the data acquisition server 120. The data acquisition server 120 operates in response to description components downloaded from the workstation 110 to receive the real-time NMR data and provide buffer storage such that no data is lost by data overrun. In some scans the data acquisition server 120 does little more than pass the acquired NMR data to the data processor server 122. However, in scans which require information derived from acquired NMR data to control the further performance of the scan, the data acquisition server 120 is programmed to produce such information and convey it to the pulse sequence server 118. For example, during prescans NMR data is acquired and used to calibrate the pulse sequence performed by the pulse sequence server 118. Also, navigator signals may be acquired during a scan and used to adjust RF or gradient system operating parameters or to control the view order in which k-space is sampled. And, the data acquisition server 120 may be employed to process NMR signals used to detect the arrival of contrast agent in an MRA scan. In all these examples the data acquisition server 120 acquires NMR data and processes it in real-time to produce information which is used to control the scan.

The data processing server 122 receives NMR data from the data acquisition server 120 and processes it in accordance with description components downloaded from the workstation 110. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc. As will be described in more detail below, the present invention is implemented by the MRI system in response to a program executed by the data processing server 122.

Images reconstructed by the data processing server 122 are conveyed back to the workstation 110 where they are stored. Real-time images are stored in a data base memory cache (not shown) from which they may be output to operator display 112 or a display 142 which is located near the magnet assembly 130 for use by attending physicians. Batch mode images or selected real time images are stored in a host database on disc storage 144. When such images have been reconstructed and transferred to storage, the data processing server 122 notifies the data store server 123 on the workstation 110. The workstation 110 may be used by an operator to archive the images, produce films, or send the images via a network to other facilities.

Figure 10:
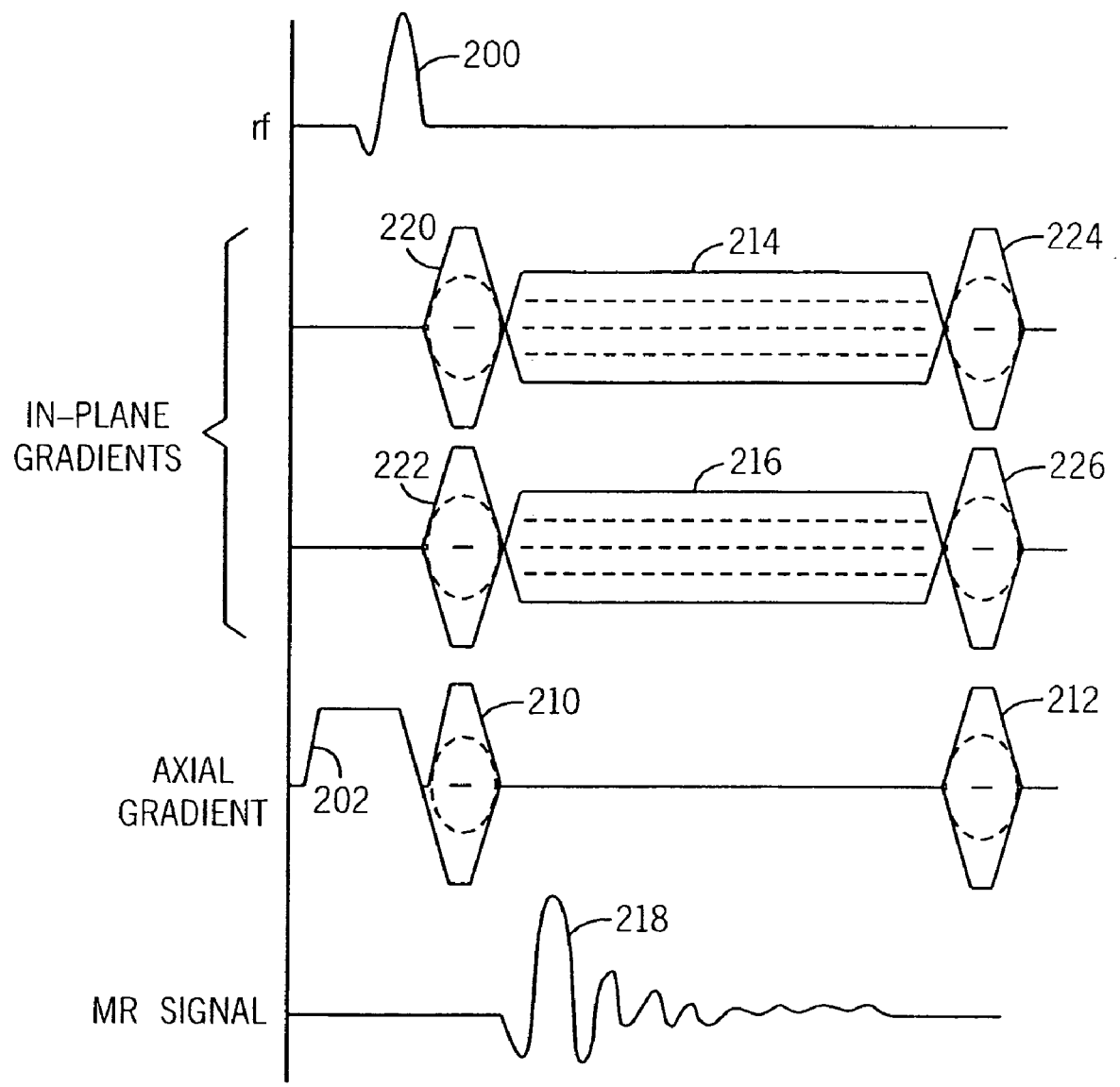
FIG. 10 is a pulse sequence used in the MRI system of FIG. 9 to practice one embodiment of the invention.
Figure 11:
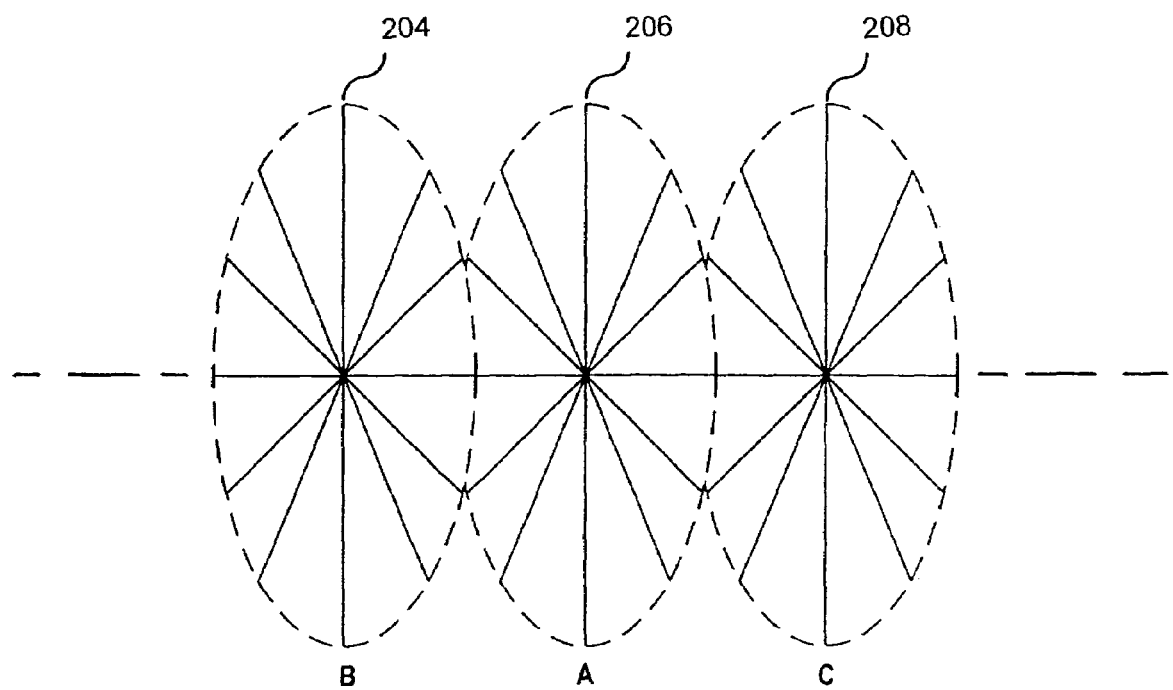
FIG. 11 is a pictorial representation of the k-space data sampled using the pulse sequence of FIG. 10.

To practice the preferred embodiment of the invention NMR data is acquired using a projection reconstruction, or radial, pulse sequence such as that shown in FIG. 10. This is a fast gradient-recalled echo pulse sequence in which a selective, asymmetrically truncated sinc rf excitation pulse 200 is produced in the presence of a slice-select gradient 202. This pulse sequence may be used to acquire a single 2D slice by sampling in a single k-space circular plane, or it may be used to sample a plurality of circular k-space planes as shown at 204, 206 and 208 in FIG. 11. When multiple 2D slices are acquired the gradient 202 is a slab select gradient followed by a phase encoding gradient lobe 210 and a rewinder gradient lobe 212 of opposite polarity. This axial, phase encoding gradient 210 is stepped through values during the scan to sample from each of the 2D k-space planes 204, 206 and 208.

Two in-plane readout gradients 214 and 216 are played out during the acquisition of an NMR echo signal 218 to sample k-space in a 2D plane 204, 206 or 208 along a radial trajectory. These in-plane gradients 214 and 216 are perpendicular to the axial gradient and they are perpendicular to each other. During a scan they are stepped through a series of values to rotate the view angle of the radial sampling trajectory as will be described in more detail below. Each of the in-plane readout gradients is preceded by a prephasing gradient lobe 220 and 222 and followed by a rewinder gradient lobe 224 and 226.

It should be apparent to those skilled in the art that sampling trajectories other than the preferred straight line trajectory extending from one point on the k-space peripheral boundary, through the center of k-space to an opposite point on the k-space peripheral boundary may also be used. As mentioned above, one variation is to acquire a partial NMR echo signal 203 which samples along a trajectory that does not extend across the entire extent of the sampled k-space volume. Another variation which is equivalent to the straight line projection reconstruction pulse sequence is to sample along a curved path rather than a straight line. Such pulse sequences are described, for example, in "Fast Three Dimensional Sodium Imaging", MRM, 37:706-715, 1997 by F. E. Boada, et al. and in "Rapid 3D PC-MRA Using Spiral Projection Imaging", Proc. Intl. Soc. Magn. Reson. Med. 13 (2005) by K. V. Koladia et al and "Spiral Projection Imaging: a new fast 3D trajectory", Proc. Intl. Soc. Mag. Reson. Med. 13 (2005) by J. G. Pipe and Koladia. It should also be apparent that the present invention may be employed with 3D as well as 2D versions of these sampling methods and use of the term "pixel" herein is intended to refer to a location in either a 2D or a 3D image.

The MRI system described above can be used in a wide variety of clinical applications to acquire either 2D or 3D sets of projection views that may be used to reconstruct one or more images. The image reconstruction method of the present invention is particularly useful in scans where one or more image frames are reconstructed using less than all the acquired projection views.

Figure 1:
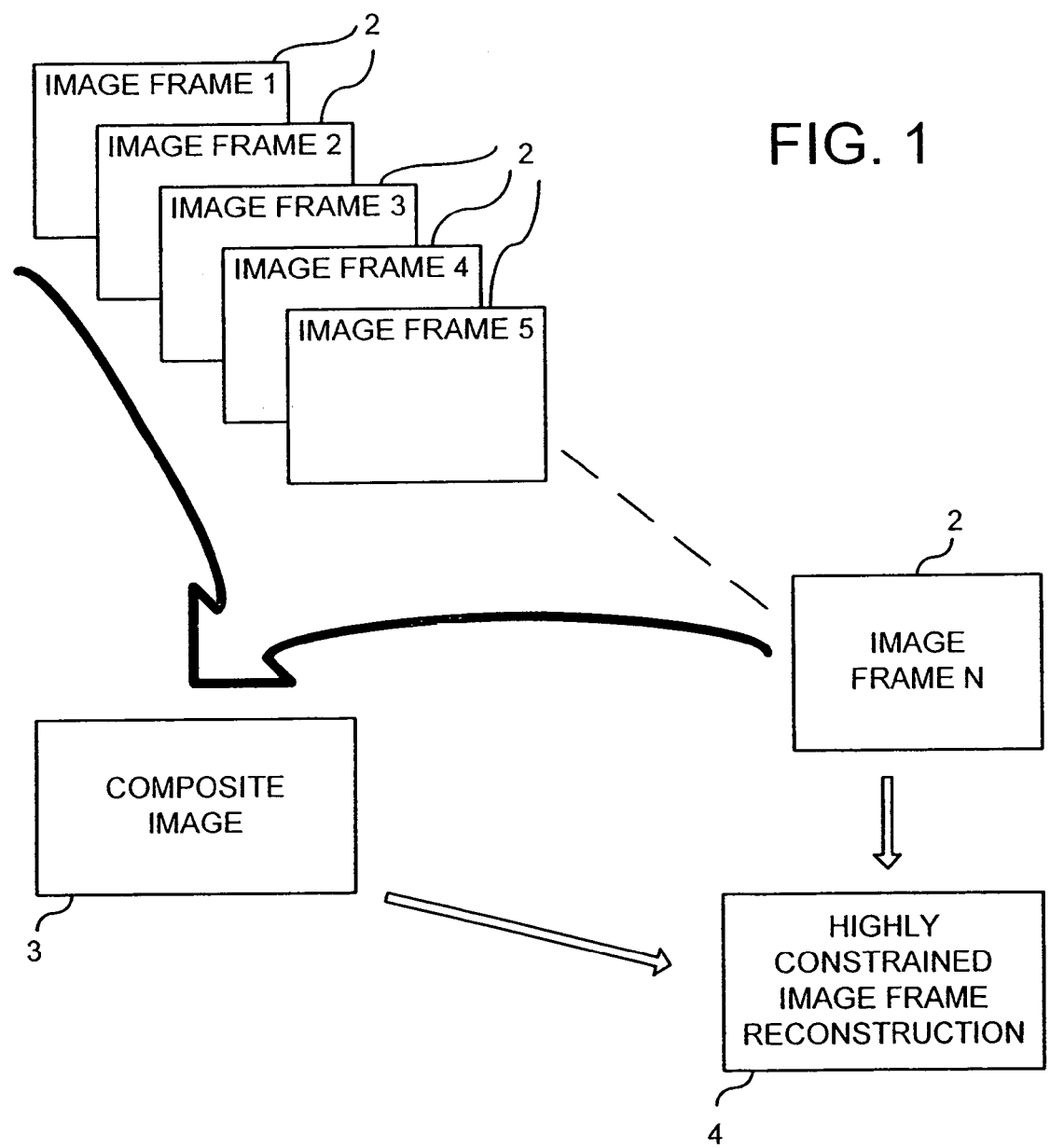
FIG. 1 is a pictorial view illustrating the application of the present invention to medical imaging applications.
Figure 2A:
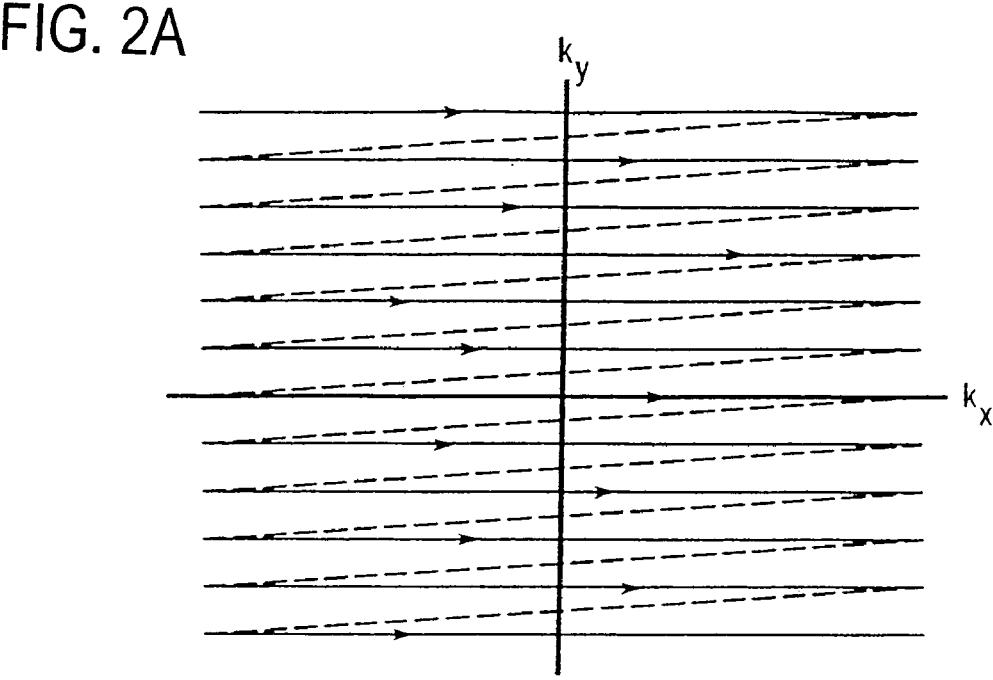
FIG. 2A is a graphic illustration of the manner in which k-space is sampled during a typical Fourier, or spin-warp, image acquisition using an MRI system.
Figure 12:
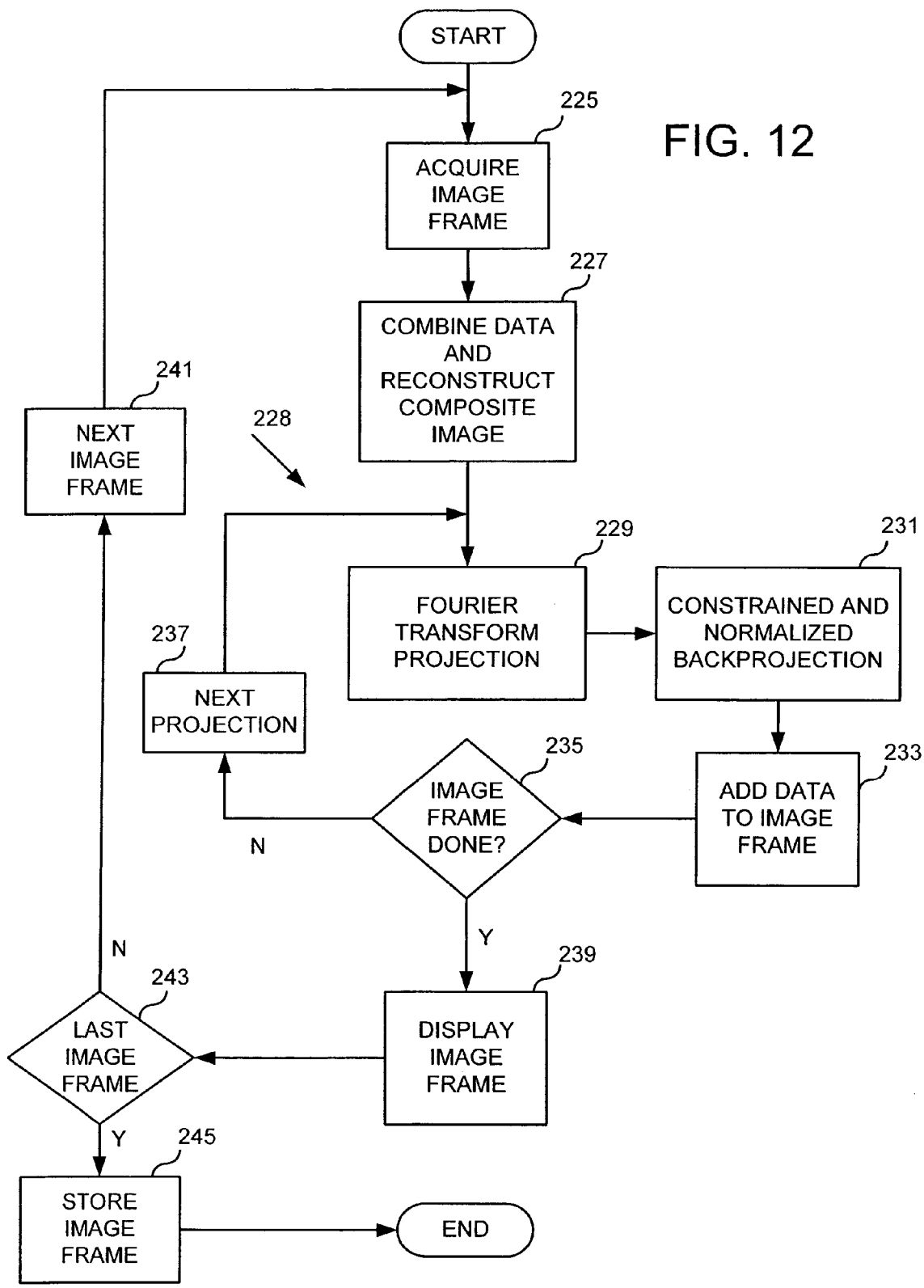
FIG. 12 is a flow chart of a preferred embodiment of the invention used in the MRI system of FIG. 9 with the pulse sequence of FIG. 10.

The first embodiment of the image reconstruction method directs the MRI system to acquire two-dimensional projection views and reconstruct a series of image frames that depict the subject over a period of time. Referring particularly to FIG. 12, a set of projection views are acquired from which an image frame is to be reconstructed as indicated at process block 225. These projection views are few in number (e.g., 10 views) and evenly distributed to sample k-space as uniformly as possible as illustrated in FIG. 2. Because of the low number of projection views that are acquired, this image frame can be acquired in a very short scan time, but because k-space is highly undersampled, streak artifacts will occur in any image reconstructed using conventional methods.

Figure 6:
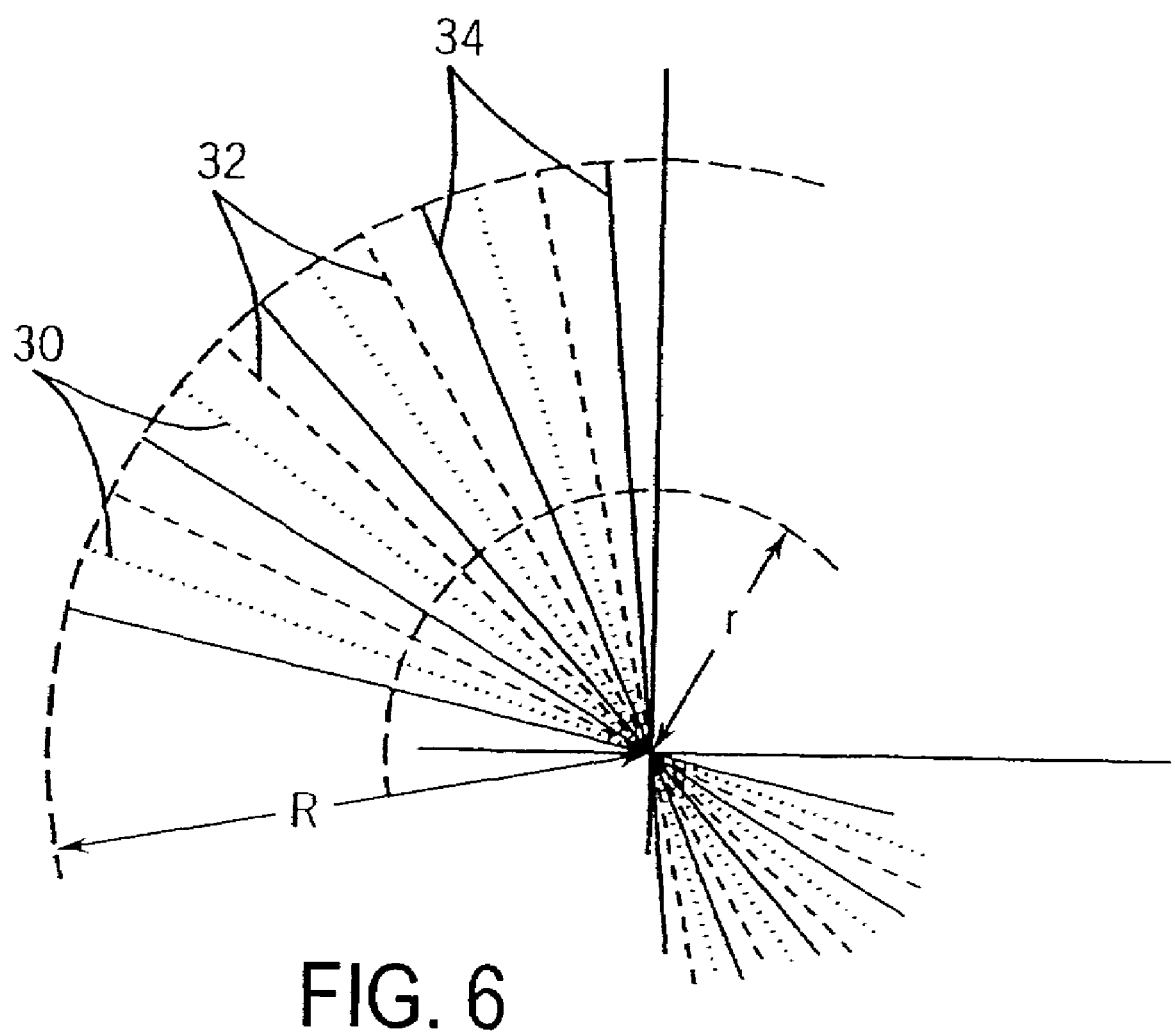
FIG. 6 is a graphic representation of interleaved projection views.

The next step as indicated at process block 227 is to combine all of the projection views that have been acquired from the subject of the examination and reconstruct a composite image. This will include projection views previously acquired which are interleaved with the views for the current image frame and which thus provides a more complete sampling of k-space. Referring to FIG. 6, for example, the current image frame projection views may sample k-space as indicated by dotted lines 30 and previously acquired image frame views may sample interleaved k-space trajectories as indicated by dashed lines 32 and lines 34. The composite image is reconstructed with all the views 30, 32 and 34 using a conventional method because a sufficient number of views are available to avoid image artifacts. In the preferred embodiment this reconstruction includes regridding the combined acquired k-space projection data into Cartesian coordinates and then performing an inverse two-dimensional Fourier transformation (2DFT) to produce the composite image.

Figure 4:
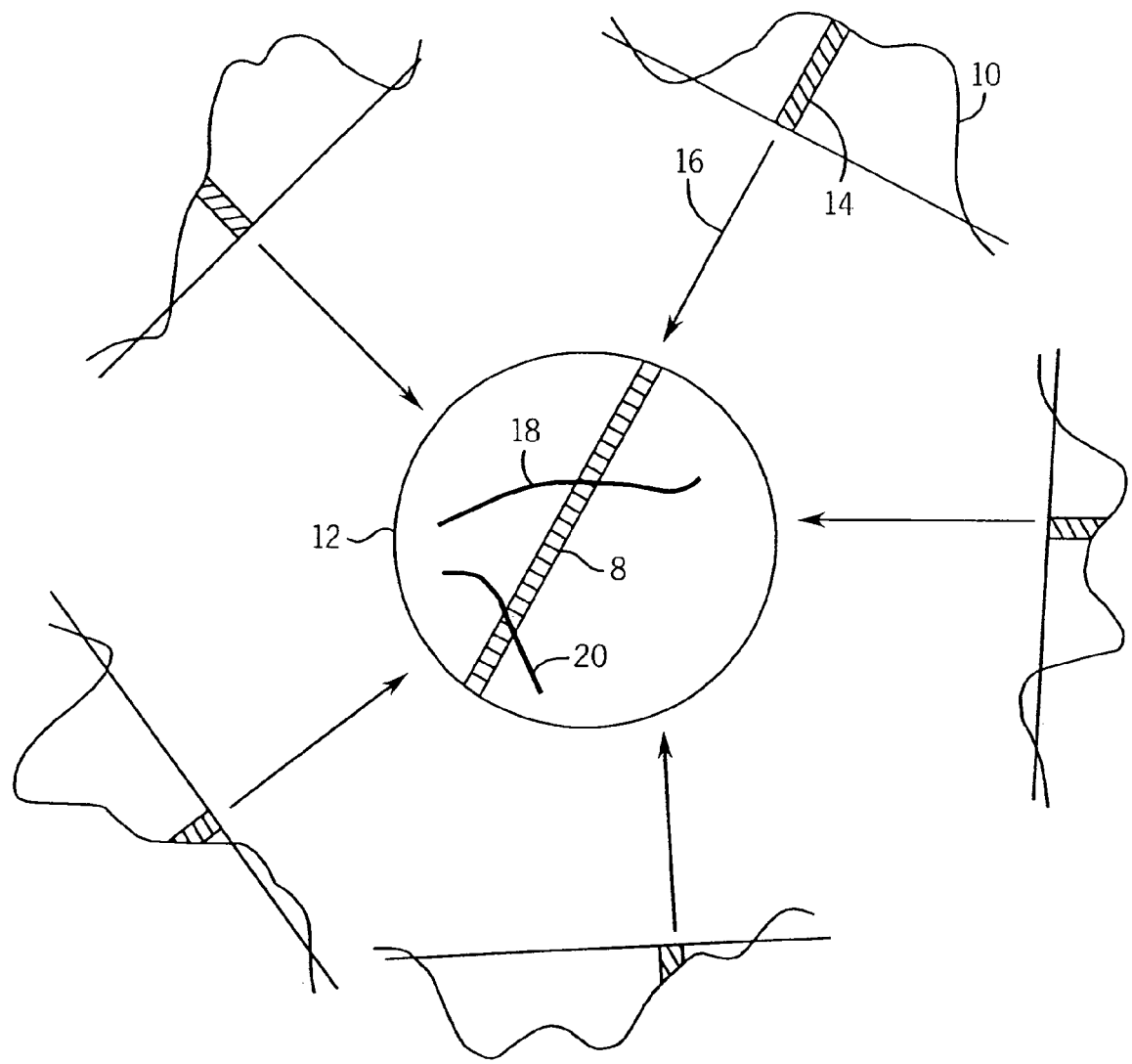
FIG. 4 is a pictorial representation of the highly constrained 2D backprojection step according to the present invention.
Figure 5:
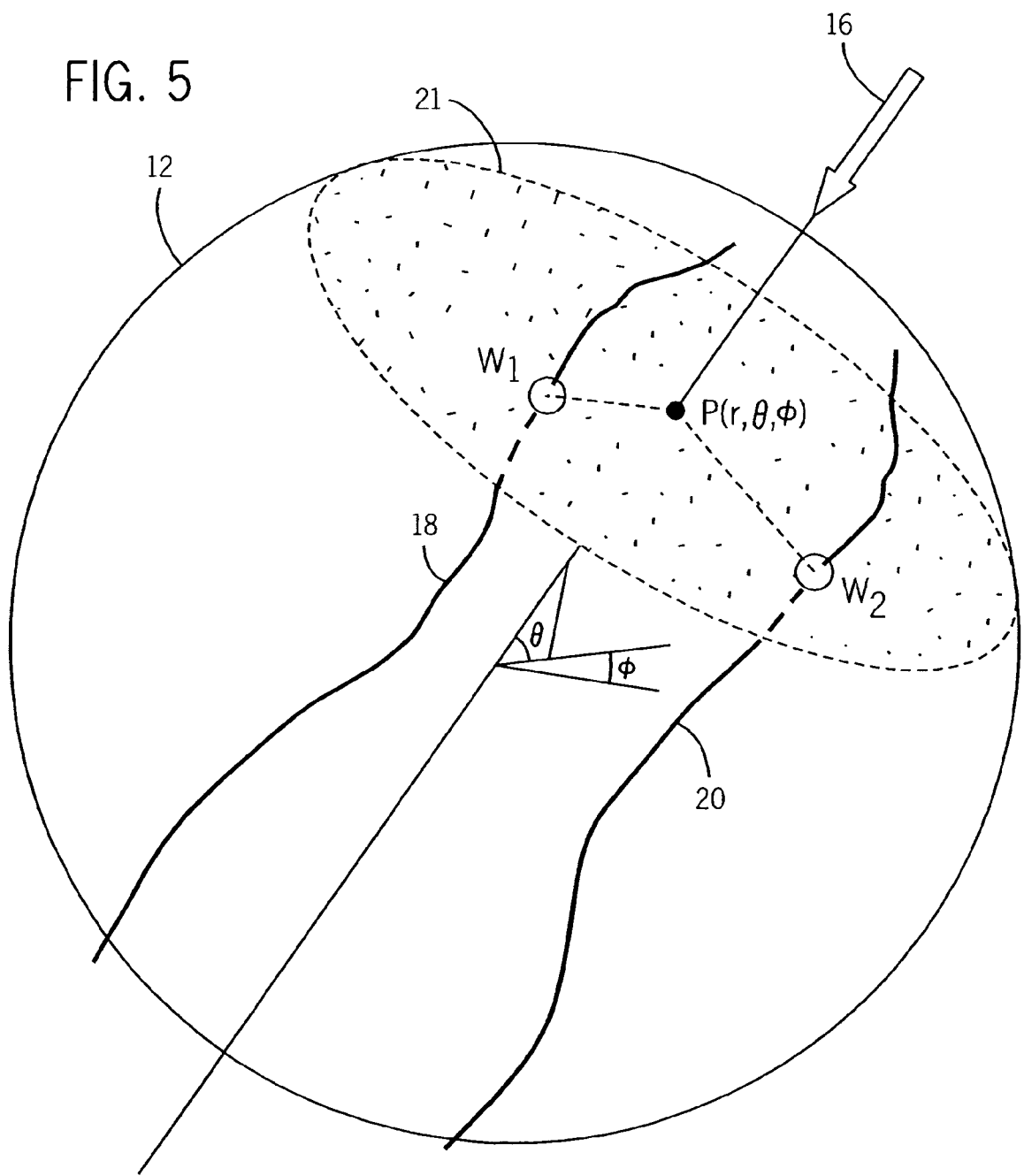
FIG. 5 is a pictorial representation of the highly constrained 3D backprojection according to the present invention.

A loop is then entered as 228, in which each projection view in the current image frame is backprojected according to the teachings of the present invention. More specifically, the k-space projection view is first transformed to Radon space by performing a one-dimensional, fast Fourier inverse transformation as indicated at process block 229. The transformed projection is then backprojected as indicated at process block 231. This highly constrained backprojection is performed as described above in equation (2) and shown in FIG. 4 using the recently reconstructed composite image. This is a highly constrained backprojection and normalization step. As indicated at process block 233, the resulting backprojected values are added to the image frame being reconstructed and a test is made at decision block 235 to determine if all of the projection views have been backprojected for the current image frame. If not, the next projection is processed as indicated at process block 237, and when all the projection views for the current image frame have been processed, the reconstructed image frame is displayed as indicated at process block 239.

Additional image frames are acquired and reconstructed as indicated at process block 241. When the last image frame is completed as determined at decision block 243, the scan stops and all the image frames are stored as indicated at process block 245. As the scan is performed image frames are thus quickly acquired and promptly reconstructed and displayed. The image frame data that is acquired during the scan is combined with previously acquired data to produce the composite image. Because the acquired views are interleaved, k-space is more densely sampled as the scan progresses, and as a result, the quality of the composite image improves, or grows, as the scan progresses. The a priori information embodied in this composite image is used to constrain and thereby improve the quality of the reconstructed image frames.

The individual time frame projection, the corresponding projection through the composite image, and the composite image itself contribute to the stochastic noise in the reconstructed image frame. It can be demonstrated that the SNR of each reconstructed image frame is dominated by the SNR of the composite image. SNR is calculated as the ratio of object signal level to the noise standard deviation within the object and CNR is calculated as the difference between the object and backgrounds signal levels divided by the standard deviation of the background noise. The overall SNR and CNR are limited by a combination of the stochastic noise and the noise due to the streak artifacts. It can be shown that the stochastic component of the SNR in the highly constrained backprojection reconstruction of the present invention is given by:

$$SNR_{HYPR} = SNR_{composite} / [1 + N_f/N_v^2 + N_{pix}/(N_p N_v^2)]^{1/2} \quad (3)$$

where $SNR_{composite}$ is the SNR in the composite image, $N_f$ is the number of image frames in the time series, $N_v$ is the number of object pixels in the projection, $N_{pix}$ is the number of pixels in the projection (e.g., 256 for 2D or 256×256 for 3D), and $N_p$ is the number of projections per image frame. If $N_p$ is on the order of 10 the SNR is dominated by $SNR_{composite}$.

Figure 13:
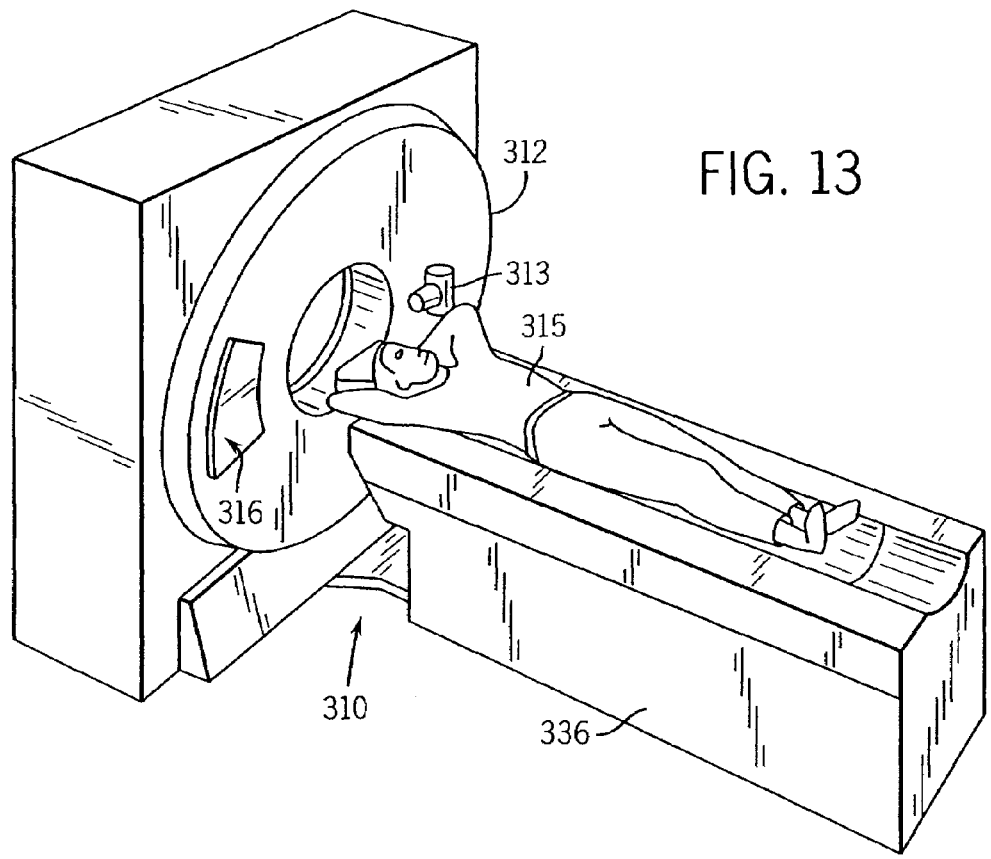
FIG. 13 is a pictorial view of a CT scanner system.
Figure 14:
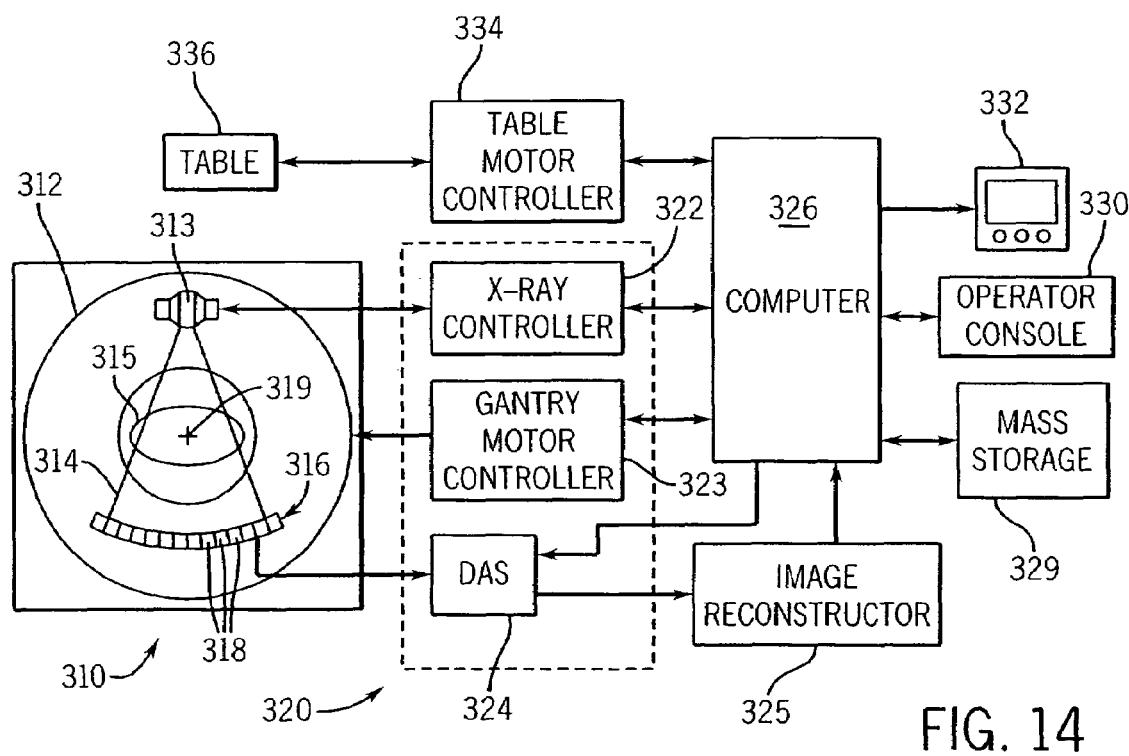
FIG. 14 is a block diagram of the CT scanner system of FIG. 13.

The present invention is also particularly applicable to other medical imaging modalities in which interleaved projection views of the subject are acquired. One such imaging modality is x-ray computed tomography. With initial reference to FIGS. 13 and 14, a computed tomography (CT) imaging system 310 includes a gantry 312 representative of a "third generation" CT scanner. Gantry 312 has an x-ray source 313 that projects a fan beam or a cone beam of x-rays 314 toward a detector array 316 on the opposite side of the gantry. The detector array 316 is formed by a number of detector elements 318 which together sense the projected x-rays that pass through a medical patient 315. Each detector element 318 produces an electrical signal that represents the intensity of an impinging x-ray beam and hence the attenuation of the beam as it passes through the patient. During a scan to acquire x-ray projection data, the gantry 312 and the components mounted thereon rotate about a center of rotation 319 located within the patient 315.

The rotation of the gantry and the operation of the x-ray source 313 are governed by a control mechanism 320 of the CT system. The control mechanism 320 includes an x-ray controller 322 that provides power and timing signals to the x-ray source 313 and a gantry motor controller 323 that controls the rotational speed and position of the gantry 312. A data acquisition system (DAS) 324 in the control mechanism 320 samples analog data from detector elements 318 and converts the data to digital signals for subsequent processing. An image reconstructor 325, receives sampled and digitized x-ray data from the DAS 324 and performs high speed image reconstruction according to the method of the present invention. The reconstructed image is applied as an input to a computer 326 which stores the image in a mass storage device 329.

The computer 326 also receives commands and scanning parameters from an operator via console 330 that has a keyboard. An associated display 332 allows the operator to observe the reconstructed image and other data from the computer 326. The operator supplied commands and parameters are used by the computer 326 to provide control signals and information to the DAS 324, the x-ray controller 322 and the gantry motor controller 323. In addition, computer 326 operates a table motor controller 334 which controls a motorized table 336 to position the patient 315 in the gantry 312.

Like the MRI system, the CT system has many different clinical applications in which either 2D or 3D sets of projection views are acquired and used to reconstruct one or more images of the patient. Whereas the projection views acquired by the MRI system are comprised of k-space (or Fourier space) samples, the projection views acquired by the CT system are comprised of Radon space samples. Image reconstruction using data acquired with a CT system necessarily requires transformation from Radon space to real space.

Figure 2B:
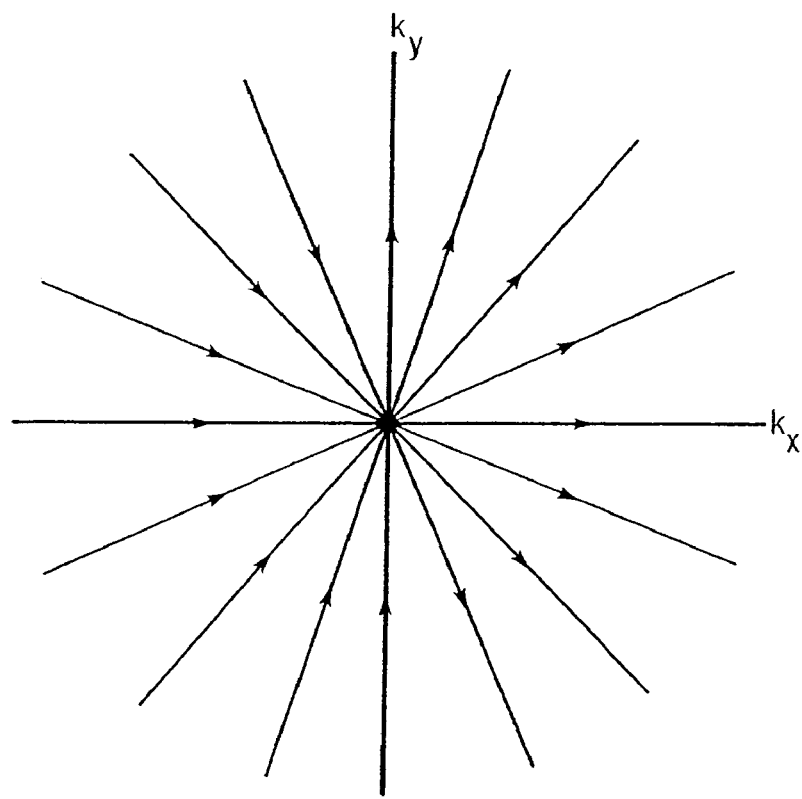
FIG. 2B is a graphic illustration of the manner in which k-space is sampled during a typical projection reconstruction image acquisition using an MRI system.
Figure 15:
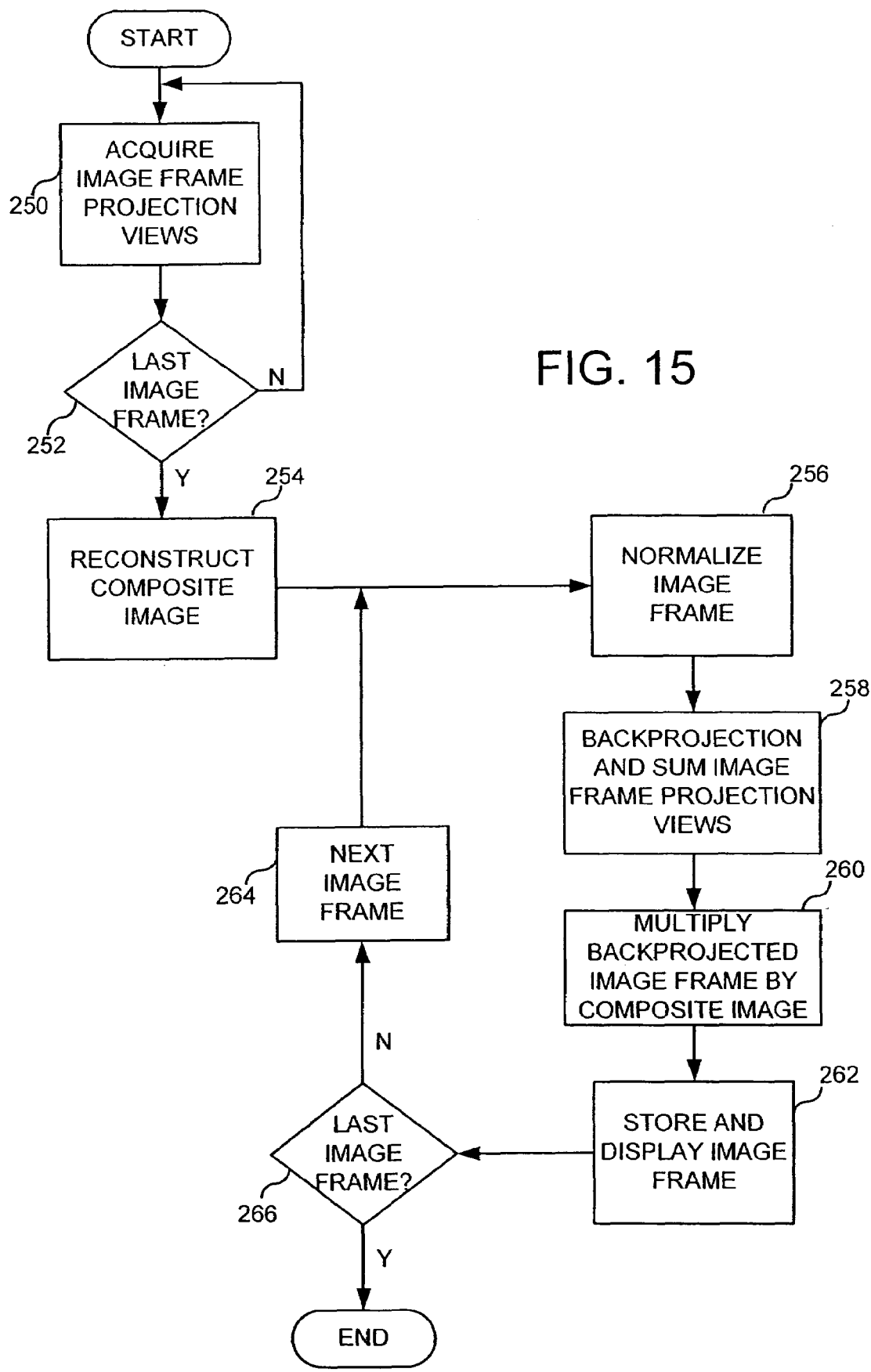
FIG. 15 is a block diagram of another embodiment of the invention using the CT scanner of FIGS. 13 and 14.

Referring particularly to FIG. 15, a second embodiment of the invention directs the CT system to acquire a series of 2D slice images. As indicated by process block 250 a set of projection views from which a 2D image frame can be reconstructed is acquired. This may be a highly undersampled acquisition in which the projection views are at equally spaced view angles that sample Radon space in a uniform manner as illustrated in FIG. 2B. In this embodiment, the data acquisition phase of the scan is completed prior to image reconstruction and the entire series of image frames are thus acquired before this phase of the scan is completed as determined at decision block 252. For example, a series of image frames may be acquired during a dynamic study in which a contrast agent flows into the region of interest. As with the first embodiment described above, the projection views acquired during this scan are interleaved as illustrated in FIG. 6 such that when they are all combined, a composite data set is formed in which Radon space is highly sampled even though each image frame data set undersamples Radon space.

As indicated at process block 254, a composite image is reconstructed from the combined projection views acquired during the acquisition phase of the scan. The sets of equally spaced projection views that form each image frame are interleaved with each other such that the projection views from a combination of image frames more fully samples Radon space and produces a higher quality image. The composite image is reconstructed from these combined projection views using a conventional image reconstruction technique such as a filtered backprojection. Whereas in the first embodiment described above, the composite image grew in quality as additional, interleaved projection views were added to it during the scan, in this second embodiment a single composite image is reconstructed in which substantially all the acquired views are used.

Figure 7:
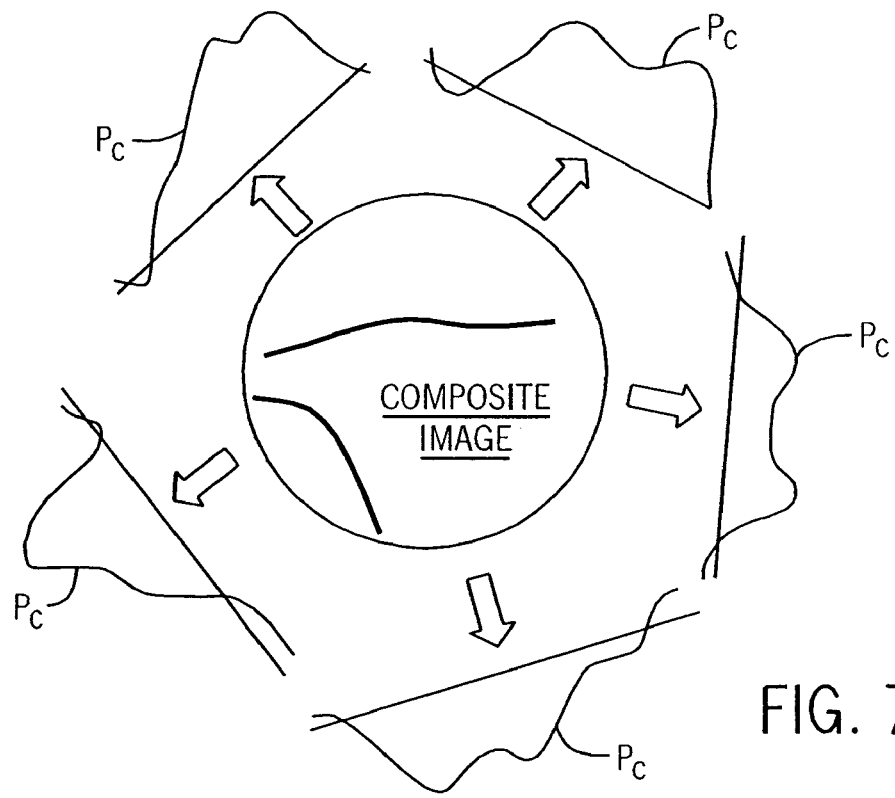
FIG. 7 is a pictorial representation of the formation of composite image projections $P_c$ used in a normalized step.
Figure 8:
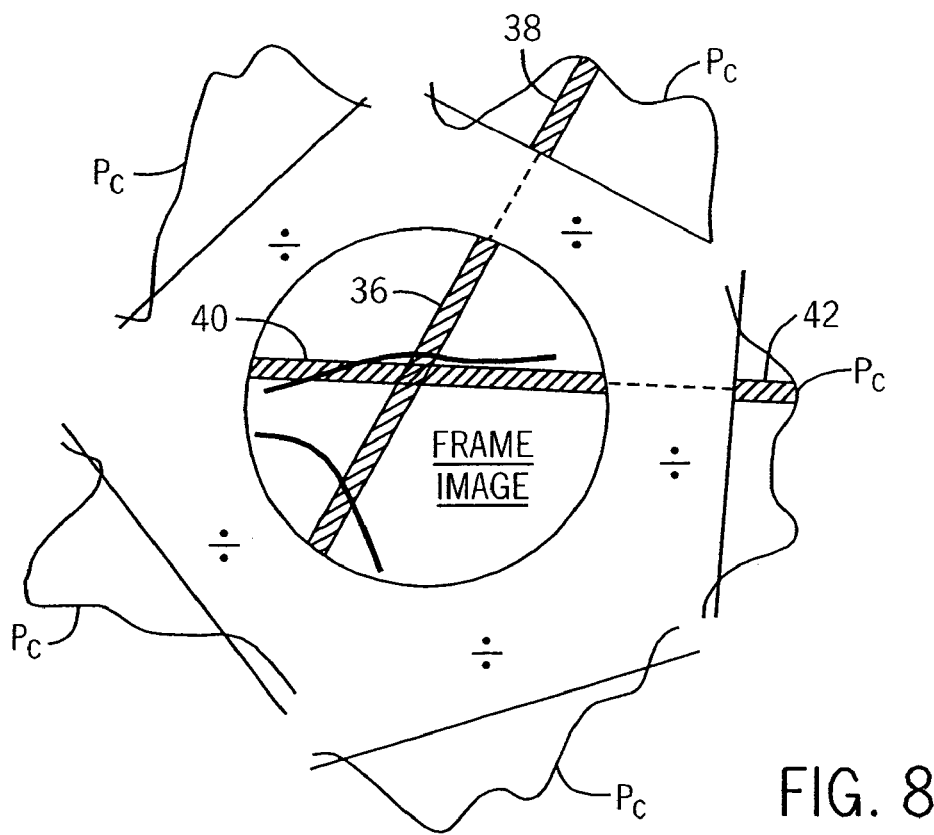
FIG. 8 is a pictorial representation of the normalization of a highly constrained image using the projections $P_c$ of FIG. 7.

While the constrained backprojection method described above with respect to FIG. 4 may be used to reconstruct each frame image, an equivalent method is used in this second embodiment. The next step indicated by process block 256 is to normalize one image frame. Normalization is performed by first calculating a set of projection views from the composite image. More specifically, a projection view of the composite image is calculated for each view angle used to form the image frame as described above with respect to FIG. 7. Each of these composite image projection values $P_c$ is then used to normalize the corresponding frame image projection values P. That is, each frame image projection value P is divided by the corresponding projection value $P_c$ derived from the composite image as discussed above with respect to FIG. 8.

Figure 3:
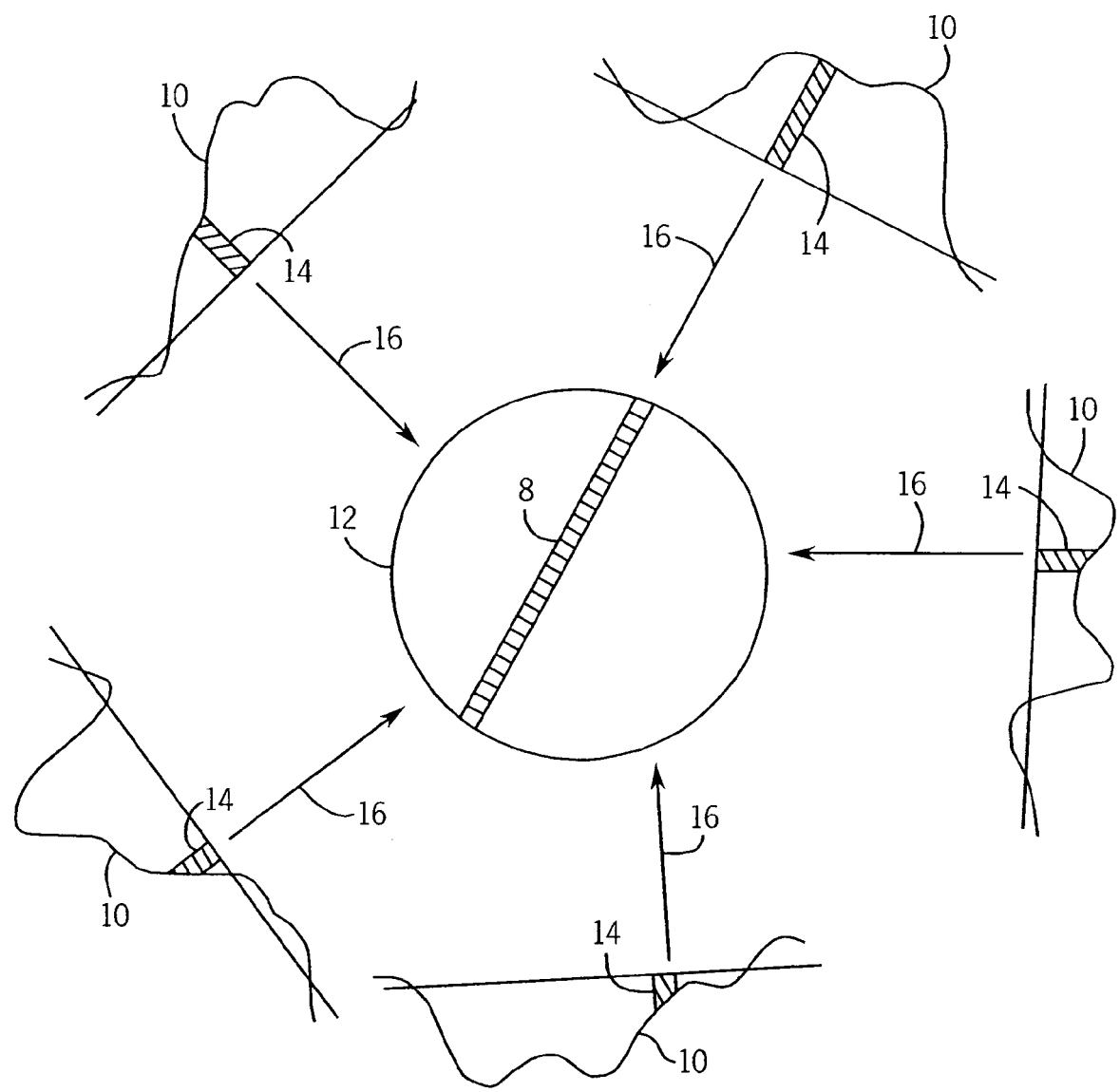
FIG. 3 is a pictorial representation of a conventional backprojection step in an image reconstruction process.

The next step is to reconstruct an image from the normalized image frame projections as indicated at process block 258. This is an unconstrained backprojection as discussed above with reference to FIG. 3 in which the ray sum attenuation value in each normalized projection is divided equally among the pixels in the ray path 8. The unconstrained backprojected values for each normalized projection view in the image frame are summed to form an unconstrained image frame data set. The filtering normally associated with conventional backprojection reconstruction is not employed during this step and because only a few projection views are used, this unconstrained image frame data set will contain many streaks and other image artifacts.

As indicated by process block 260, the next step is to multiply the unconstrained backprojected image frame data set by the composite image to form a constrained image. This is a pixel-by-pixel multiplication in which each pixel value in the unconstrained image frame data set is multiplied by the value of the corresponding pixel in the composite image. The resulting highly constrained image frame is stored and may be displayed as indicated at process block 262.

Further image frames are reconstructed as indicated at process block 264 until all the data acquired during the data acquisition phase of the scan is used as determined at decision block 266. The reconstruction phase of the scan ends at this point, although the reconstructed image frames may be further processed depending on the particular clinical application. In this embodiment the composite image is formed by all the views acquired during the scan to provide a substantial improvement in image frame SNR, but the image frames are not available in real time. Also, the image frame is constrained in real image space rather than during the Radon space-to-real image space backprojection process.

While it is preferable from an image SNR standpoint to form the composite image using all the interleaved views acquired during the scan, there are instances when it may be preferable to use less than all the acquired views. For example, during a dynamic study the object being imaged may change substantially during the scan. To better capture this change in the series of reconstructed image frames it is preferable to use views in the composite image that are acquired temporally around the same time as the views used to reconstruct the image frame. In other words, the views used to form the composite image are acquired during a time window that includes the image frame being reconstructed and a selected number of views acquired both before and after the image frame views are acquired. The size of this window is selected to provide the best tradeoff between better SNR on the one hand resulting from a wide window, and a more accurate depiction of temporal changes in the object on the other hand resulting from a narrow window. This selection can be done after the scan is completed and different window sizes for the composite image may be tried during the image reconstruction phase to find the optimal tradeoff.

Figure 16:
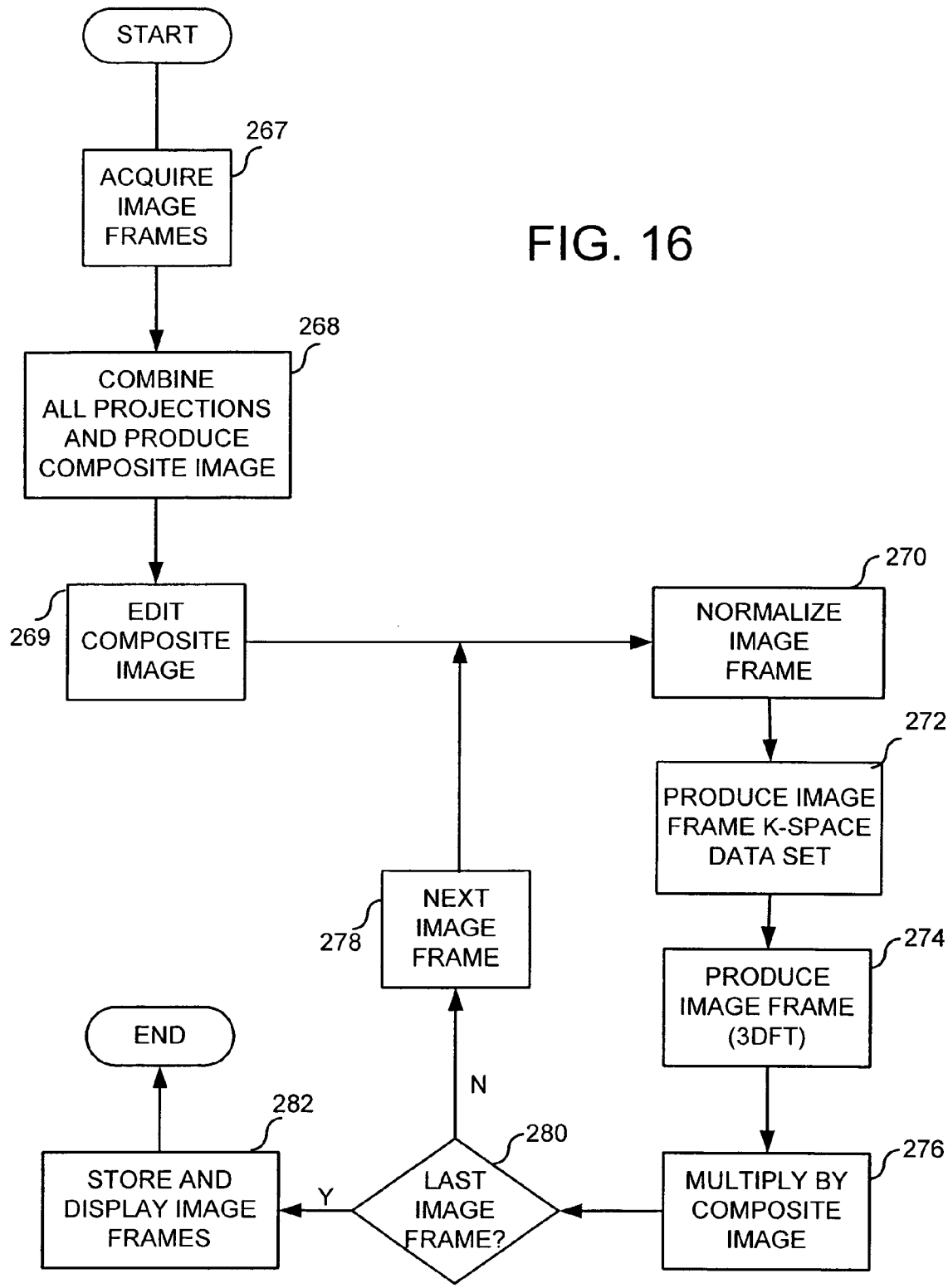
FIG. 16 is a block diagram of yet another embodiment of the invention using the CT scanner of FIGS. 13 and 14.

Referring particularly to FIG. 16, another preferred embodiment of the invention acquires a series of time resolved 3D image frames with the CT system. As indicated at process block 267, a series of 3D image frames are acquired during a period of time by acquiring cone beam projection views at equally spaced and interleaved view angles. Each set of image frame projection views is limited in number in order to improve the time resolution of each image frame and the cone beam projection views of successive image frames are interleaved with each other as in the embodiments discussed above. When the data acquisition phase of the scan is completed, cone beam projection views from successive image frames are combined and used to reconstruct a composite image as indicated at process block 268. This is a conventional cone beam image reconstruction using one of the well known techniques based on the methods disclosed by L. A. Feldkamp, L. C. Davis, and J. W. Kress, "Practical Cone Beam Algorithm," J. Opt. Soc. Am. A1, 612-619 (1984); G. Wang, T. H. Lin, P. Cheg, and D. M. Shinozaki, "A General Cone-Beam Reconstruction Algorithm," IEEE Trans. Med. Imaging 12, 486-496 (1993).

The image reconstruction according to the present invention is highly constrained by the content of the composite image. This fact is used to advantage in this embodiment where objects in the field of view are to be removed from the final image. This is done by editing the composite image as indicated at process block 269 to delete the unwanted subject matter. More specifically, the pixels corresponding to the structure to be removed is identified in the composite image. In one copy of the composite image, all pixels outside the identified region are set to zero, and in a second copy of the composite image all pixels in the identified region are set to zero. Using the first copy of the composite image which contains the unwanted structures, projections are taken along each projection angle used during the scan. These projection views of the unwanted structures are then subtracted from the acquired projection data at the corresponding view angles to remove most of the unwanted signal. The second copy of the composite image in which pixels corresponding to unwanted structures are set to zero is then used during the highly constrained reconstruction described below to suppress any remaining unwanted signals. The editing can be done manually by deleting structures such as metal objects or it may be done automatically by subtracting a mask image from the composite image. Such a mask image may be, for example, an image of the subject before injection of a contrast agent in order to remove structures from the image frames that are not affected by the contrast agent.

Referring still to FIG. 16, a loop is entered in which each of the acquired 3D image fames is reconstructed according to the teachings of the present invention. As indicated at process block 270, the first step is to normalize the acquired image frame projections. This is accomplished in exactly the same manner as described above for process block 256 in FIG. 16. That is, composite image projections are calculated for each image frame projection angle and the image frame projection values P are then divided by their corresponding composite image projection values $P_c$.

Using the normalized image frame projections, the next step as indicated at process block 272 is to produce a 3D k-space image frame data set using all the cone beam projection views in one of the acquired image frames. While there are a number of ways to do this, the preferred method is that disclosed by Guang-Hong Chen in U.S. patent application Ser. No. 10/861,579 filed on Jun. 4, 2004 and entitled "Fourier Space Tomographic Image Reconstruction Method" which is incorporated herein by reference. The divergent, cone beam projection views are thus converted to k-space samples on a three-dimensional Cartesian grid.

As indicated at process block 274, the resulting image frame k-space data set is transformed to real space by next performing an inverse, three-dimensional Fourier transformation (3DFT). This is a conventional transformation commonly used in MRI systems and a 3D unconstrained image frame results. However, because of the limited number of view angles employed in a single image frame, this unconstrained image frame will contain artifacts and noise.

The artifact ridden, unconstrained image frame is constrained using the composite image. In this particular embodiment, the unconstrained image frame is first normalized as indicated by process block 274 and then constrained by multiplying each pixel value therein by the corresponding pixel value in the composite image as indicated by process block 276. This is repeated for each acquired image frame as indicate by process block 278. When the last image frame is reconstructed as determined at decision block 280, the image frames are stored and available for display as indicated at process block 282.

In the above-described embodiments the a priori information used to reconstruct the composite image results from the acquisition of a plurality of image frames at interleaved projection views. There are other clinical applications of the present invention, however, in which a priori information is available for a quality composite image without acquiring additional projection views. One of these is data acquired with a positron emission tomography (PET) scanner.

Figure 17:
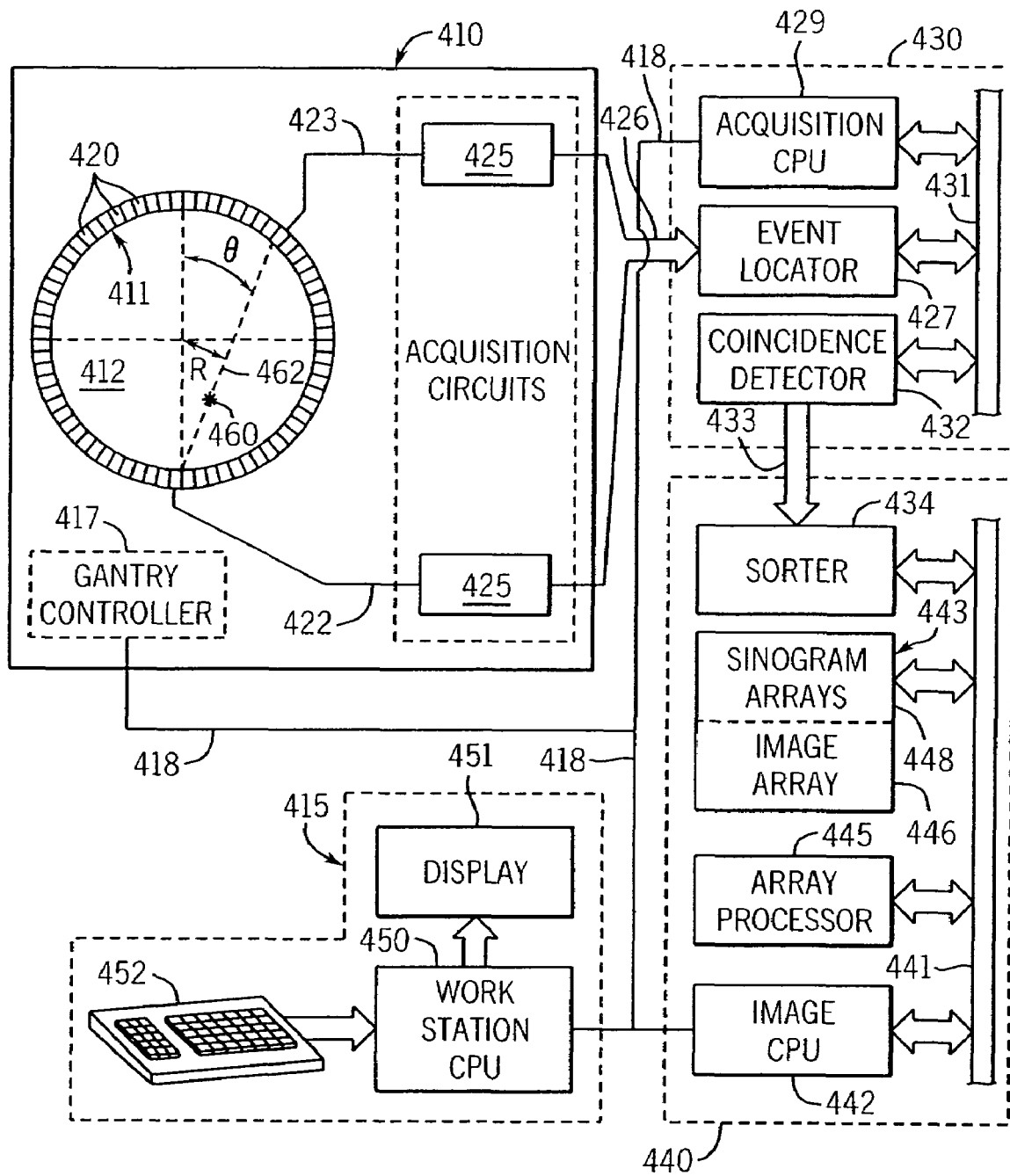
FIG. 17 is a block diagram of a positron emission tomography (PET) scanner.

Referring particularly to FIG. 17, the PET scanner system includes a gantry 410 which supports a detector ring assembly 411 about a central opening, or bore 412. A gantry controller 417 is mounted within the gantry 410 and is responsive to commands received from an operator work station 415 through a second serial communication link 418 to operate the gantry.

The detector ring 411 is comprised of detector blocks 420. Each block 420 includes a set of scintillator crystal photomultiplier tubes. A set of acquisition circuits 425 are mounted within the gantry 410 to receive the signals from each of the modules 420 in the detector ring 411. The acquisition circuits 425 determine the event coordinates within each block of scintillator crystals and these coordinates (x,z), along with the sum of the crystal block signals are digitized and sent through a cable 426 to an event locater circuit 427 housed in a separate cabinet 428. Each acquisition circuit 425 also produces an event detection pulse (EDP) which indicates the exact moment the scintillation event took place.

The event locator circuits 427 form part of a data acquisition processor 430 which periodically samples the signals produced by the acquisition circuits 425. The processor 430 has a backplane bus structure 431 and an acquisition CPU 429 which controls communications on this bus 431 and links the processor 430 to the local area network 418. The event locator 427 is comprised of a set of separate circuit boards which each connect to the cable 426 and receive signals from corresponding acquisition circuits 425 in the gantry 410. The event locator 427 synchronizes the event with the operation of the processor 430 by detecting the event pulse (EDP) produced by an acquisition circuit 425, and converting it into an 8-bit time marker which indicates when within the current sample period the scintillation event took place. Also, this circuit 427 discards any detected events if the total energy of the scintillation is outside the range of 511 keV±20%. During each sample period, the information regarding each valid event is assembled into a set of digital numbers that indicate precisely when the event took place and the position of the scintillator crystal which detected the event. This event data packet is conveyed to a coincidence detector 432 which is also part of the data acquisition processor 430.

The coincidence detector 432 accepts the event data packets from the event locators 427 and determines if any two of them are in coincidence. Events which cannot be paired are discarded, but coincident event pairs are located and recorded as a coincidence data packet that is conveyed through a serial link 433 to a sorter 434. Each coincidence data packet includes a pair of digital numbers which precisely identify the addresses of the two scintillator crystals that detected the event. From these, the location and angle of the ray path that produced the coincidence event can be determined.

The sorter 334 is a circuit which forms part of an image reconstruction processor 340. The image reconstruction processor 440 is formed about a backplane bus 441. An image CPU 442 controls the backplane bus 441 and it links the processor 440 to the local area network 418. A memory module 443 also connects to the backplane 441 and it stores the data used to reconstruct images as will be described in more detail below. An array processor 445 also connects to the backplane 441 and it operates under the direction of the image CPU 442 to perform the image reconstruction using the data in memory module 443. The resulting image array 446 is stored in memory module 443 and is output by the image CPU 442 to the operator work station 415.

The function of the sorter 434 is to receive the coincidence data packets and generate from them memory addresses for the efficient storage of the coincidence data. The set of all coincidence event rays that point in the same direction (θ) and pass through the scanner's field of view is a complete projection, or "view". The distance (R) between a particular ray path in a projection view and the center of the field of view locates that ray within the view. As shown in FIG. 17, for example, an event 460 occurs along a projection ray 462 which is located in a view at the projection angle θ and the distance R. The sorter 434 counts all of the events that occur on this projection ray (R,θ) during the scan by sorting out the coincidence data packets that indicate an event at the two scintillator crystals lying on this projection ray. During an emission scan, the coincidence counts are organized in memory 443 as a set of two-dimensional arrays, one for each axial image, and each having as one of its dimensions the projection angle θ and the other dimension the distance R. This θ by R map of the measured coincidence events is called a histogram, or more commonly the sinogram array 448.

Coincidence events occur at random and the sorter 434 quickly determines the θ and R values from the two scintillator crystal addresses in each coincidence data packet and increments the count of the corresponding sinogram array element. At the completion of the emission scan, the sinogram array 448 stores the total number of annihilation events which occurred along each ray. The number of such annihilation events indicates the number of positron electron annihilation events that occurred along the ray R, θ during the emission scan and within a few minutes hundreds of thousands of events are typically recorded. These numbers are used to reconstruct a tomographic image.

It can be appreciated that the quality of a PET image will depend to a great extent on the number of scintillation events that are allowed to accumulate in the sinogram 448. The longer the scan continues, the larger the number of detected scintillation events and the higher the quality of the reconstructed image.

Figure 18:
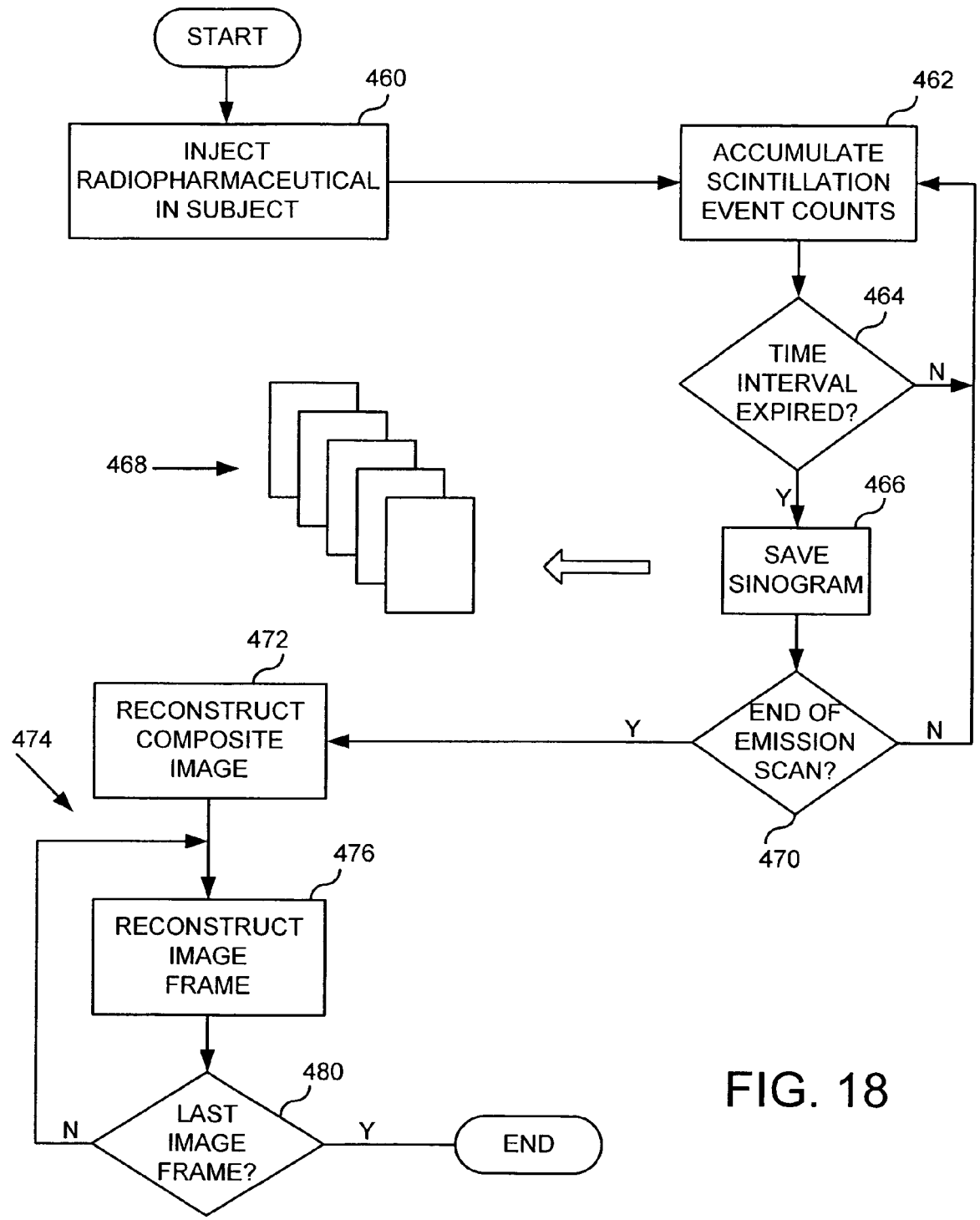
FIG. 18 is a flow chart of yet another embodiment of the invention using the PET scanner of FIG. 17.

Referring particularly to FIG. 18, the present invention is employed by the PET scanner to perform a time-resolved emission scan. The emission scan begins as indicated at process block 460 by injecting a radionuclide into the subject of the examination. The radionuclides most often employed in diagnostic imaging are fluorine-18 ($^{18}$F), carbon-11 ($^{11}$C), nitrogen-13 ($^{13}$N), and oxygen-15 ($^{15}$O). These are employed as radioactive tracers called "radiopharmaceuticals" by incorporating them into substances, such as glucose or carbon dioxide. The radiopharmaceuticals are injected in the patient and become involved in such processes as glucose metabolism, fatty acid metabolism and protein synthesis.

The subject is placed in the bore 412 of the PET scanner and scintillation events are detected and counted as indicated at process block 462. As described above, the scintillation events are detected, sorted and stored in sinogram 448 as counts for each ray R in the projection views θ. Events are counted and accumulated for a relatively short time interval as determined at decision block 464. This time interval determines the time resolution of the emission scan and it may be, for example, one-tenth the duration of a conventional emission scan. As indicated at process block 466, when the time interval expires the accumulated scintillation event counts are saved as a time interval sinogram 468.

The emission scan continues and the accumulated sinogram count is saved after each time interval until the end of the scan is detected at decision block 470. End of scan may be a preset time or a preset number of time intervals. In either case, a plurality of time interval sinograms 468 will be produced during the emission scan and the last sinogram 468 will store the total count for the entire emission scan.

The image reconstruction phase of the scan now begins, and during this phase an image frame indicative of the uptake of the radiopharmaceutical at the end of each time interval is reconstructed. First, as indicated at process block 472, a composite image is reconstructed. This is a conventional backprojection reconstruction using the last sinogram 468 saved during the emission scan. This contains the accumulated scintillation events for the entire emission scan and the image quality will be the best possible.

A loop is then entered at 474 in which time resolved image frames are reconstructed using this composite image More specifically, as indicated at process block 476 a highly constrained backprojection of each stored time interval sinogram 468 is performed. This highly constrained backprojection is performed as described above in Eq. (2) and shown in FIG. 4 using the recently reconstructed composite image. This is a highly constrained backprojection and normalization step in which the accumulated scintillation count for each ray R in each view θ of the time interval sinogram 468 is projected back along its ray path and multiplied by the corresponding pixel value in the composite image and divided by the sum of the composite pixel values along the same ray path. The resulting backprojected values for each ray path R, θ are added to the image frame being reconstructed.

The image frame reconstruction process 476 is repeated until image frames corresponding to each time interval sinogram 468 is produced as detected at decision block 480. As a result, a series of image frames are produced which indicate the uptake of the radiopharmaceutical at each time interval during the emission scan. By using the higher quality composite image in the highly constrained backprojection reconstruction, the image quality of each image frame is substantially improved over conventional images reconstructed using sinograms having low annihilation event counts.

In this PET scanner embodiment the composite image is not formed using additional interleaved views acquired during the scan, but rather, by combining the data acquired at the same set of views during each of a plurality of time intervals during the scan. Composite image quality is improved in this embodiment by increasing the SNR of each view rather than increasing the number of views as in the prior embodiments described above. This same strategy can also be used in x-ray CT, for example, to reduce patient x-ray exposure without reducing image quality. In such an embodiment a series of image frames are acquired using the same set of projection angles in each image frame. However, the x-ray dose is lowered to reduce the exposure for the patient. The frame image SNR is retained by using the highly constrained reconstruction method of the present invention with a composite image produced by combining the low-dose attenuation measurements made during each image frame acquisition. Rather than adding coincidence event counts as in the PET scanner embodiment, the "combination" in this x-ray embodiment is the average of all the corresponding attenuation measurements in acquired frame images.

This same image reconstruction strategy can be used in reconstructing images acquired with single photon emission computed tomography (SPECT) systems. As with PET scanners, SPECT systems accumulate counts of detected photons emitted from the subject along different ray paths. During a scan a gamma camera is moved slowly to accumulate counts at different view angles. Using the present invention a series of image frames may be acquired by moving the gamma camera more quickly and repeatedly through the same series of view angles. A lower count is accumulated at each view angle so as not to increase total scan time, but the SNR of each reconstructed image frame is maintained using a composite image that is formed by adding all the counts together for each view angle.

Figure 19:
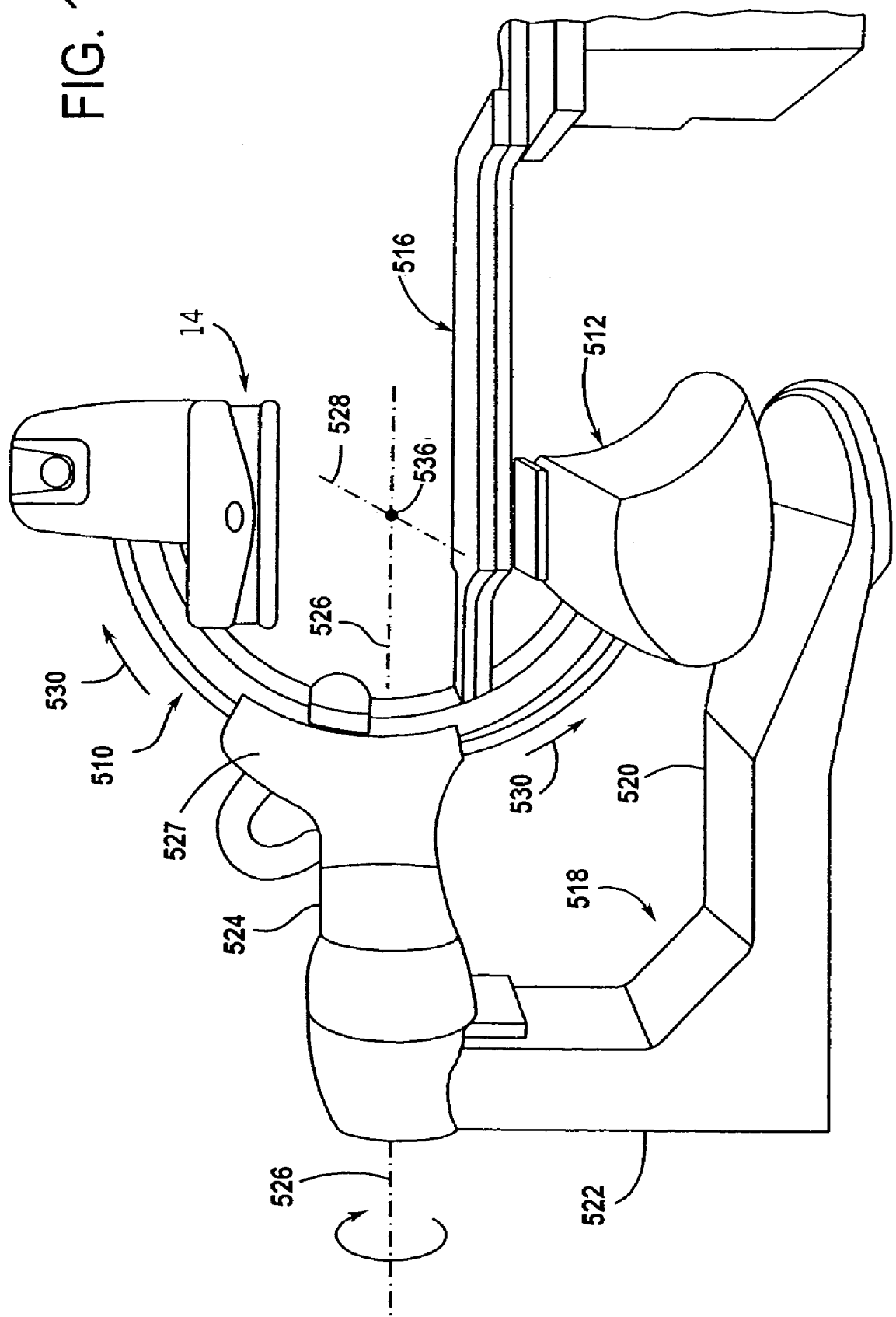
FIG. 19 is a pictorial view of a C-arm x-ray system which employs the present invention.
Figure 20:
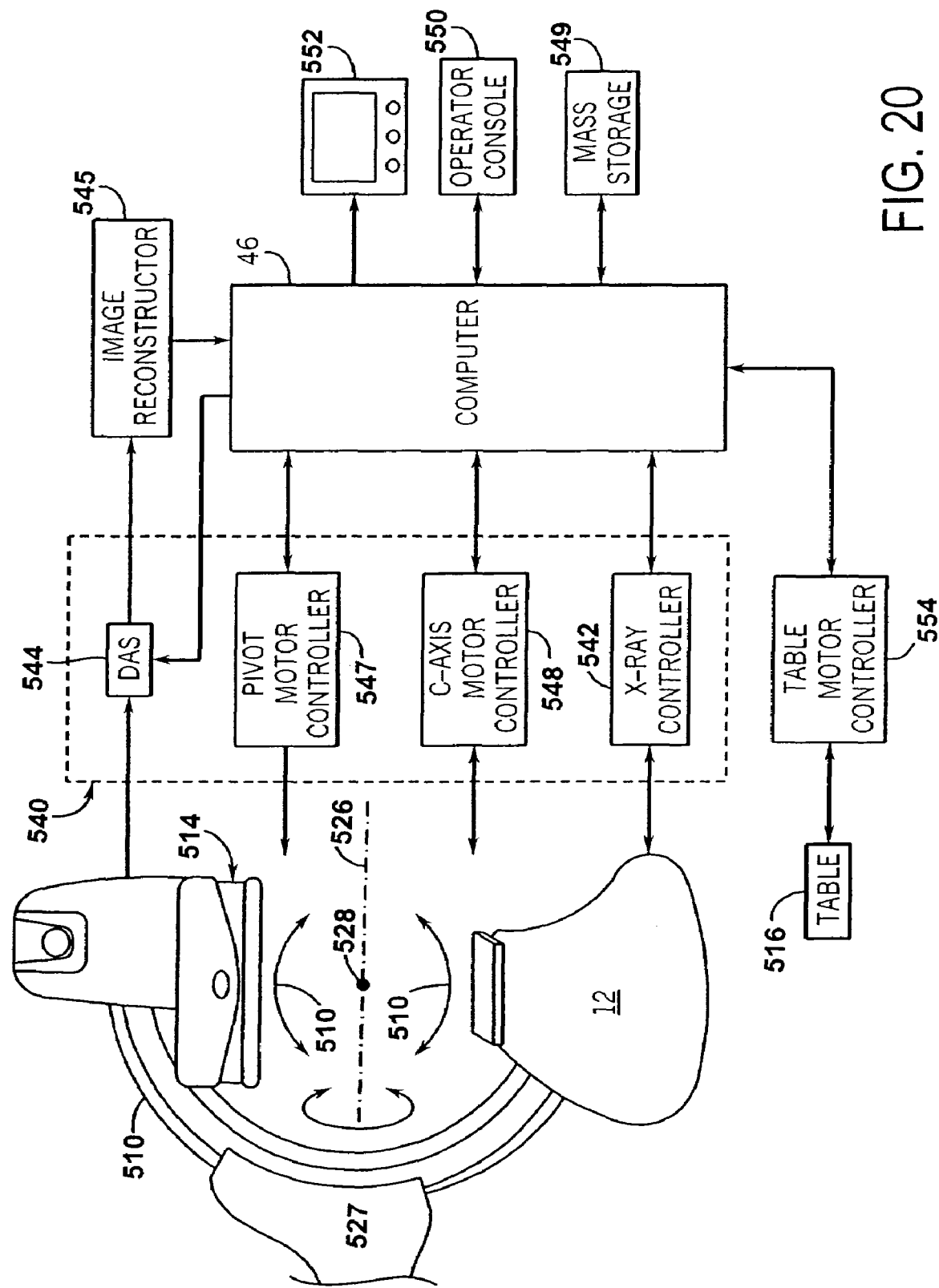
FIG. 20 is a block diagram of the C-arm x-ray system of FIG. 19.

Referring particularly to FIGS. 19 and 20, an embodiment of the invention employed to reconstruct tomosynthesis images employs an x-ray system that is designed specifically for use in connection with interventional procedures. It is characterized by a gantry having a C-arm 510 which carries an x-ray source assembly 512 on one of its ends and an x-ray detector array assembly 514 at its other end. The gantry enables the x-ray source 512 and detector 514 to be oriented in different positions and angles around a patient disposed on a table 516, while enabling a physician access to the patient.

The gantry includes an L-shaped pedestal 518 which has a horizontal leg 520 that extends beneath the table 516 and a vertical leg 522 that extends upward at the end of the horizontal leg 520 that is spaced from of the table 516. A support arm 524 is rotatably fastened to the upper end of vertical leg 522 for rotation about a horizontal pivot axis 526. The pivot axis 526 is aligned with the centerline of the table 516 and the arm 524 extends radially outward from the pivot axis 526 to support a C-arm drive assembly 527 on its outer end. The C-arm 510 is slidably fastened to the drive assembly 527 and is coupled to a drive motor (not shown) which slides the C-arm 510 to revolve it about a C-axis 528 as indicated by arrows 530. The pivot axis 526 and C-axis 28 intersect each other at an isocenter 536 located above the table 516 and they are perpendicular to each other.

The x-ray source assembly 512 is mounted to one end of the C-arm 510 and the detector array assembly 514 is mounted to its other end. As will be discussed in more detail below, the x-ray source 512 emits a cone beam of x-rays which are directed at the detector array 514. Both assemblies 512 and 514 extend radially inward to the pivot axis 526 such that the center ray of this cone beam passes through the system isocenter 536. The center ray of the cone beam can thus be rotated about the system isocenter around either the pivot axis 526 or the C-axis 528, or both during the acquisition of x-ray attenuation data from a subject placed on the table 516.

Figure 21:
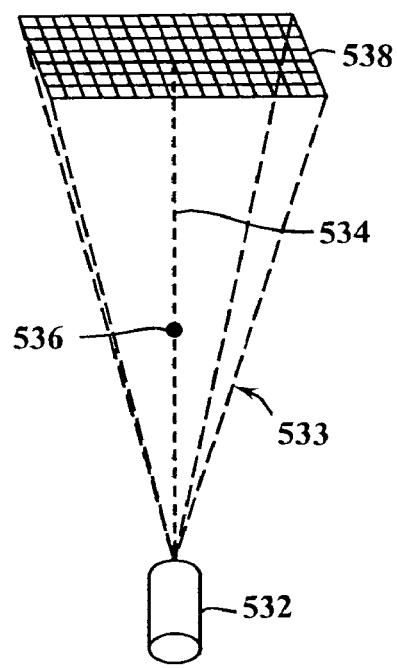
FIG. 21 is a pictorial view of the x-ray source and detector in the C-arm x-ray system of FIG. 19.

As shown in FIG. 21, the x-ray source assembly 512 contains an x-ray source 532 which emits a cone beam 533 of x-rays when energized. The center ray 534 passes through the system isocenter 536 and impinges on a two-dimensional flat panel digital detector 38 housed in the detector assembly 514. The detector 538 is a 2048 by 2048 element two-dimensional array of detector elements having a size of 41 cm by 41 cm.

Each element produces an electrical signal that represents the intensity of an impinging x-ray and hence the attenuation of the x-ray as it passes through the patient. During a scan the x-ray source 532 and detector array 538 are rotated about the system isocenter 536 to acquire x-ray attenuation projection data from different angles. The detector array is able to acquire 30 projections, or views, per second and this is the limiting factor that determines how many views can be acquired for a prescribed scan path and speed.

Referring particularly to FIG. 20, the rotation of the assemblies 512 and 514 and the operation of the x-ray source 32 are governed by a control mechanism 540 of the CT system. The control mechanism 540 includes an x-ray controller 542 that provides power and timing signals to the x-ray source 532. A data acquisition system (DAS) 544 in the control mechanism 540 samples data from detector elements 538 and passes the data to an image reconstructor 545. The image reconstructor 545, receives digitized x-ray data from the DAS 544 and performs high speed image reconstruction according to the methods of the present invention. The reconstructed image is applied as an input to a computer 546 which stores the image in a mass storage device 549 or processes the image further.

The control mechanism 540 also includes pivot motor controller 547 and a C-axis motor controller 548. In response to motion commands from the computer 546 the motor controllers 547 and 548 provide power to motors in the x-ray system that produce the rotations about respective pivot axis 526 and C-axis 528. A program executed by the computer 546 generates motion commands to the motor drives 547 and 548 to move the assemblies 512 and 514 in a prescribed scan path.

The computer 546 also receives commands and scanning parameters from an operator via console 550 that has a keyboard and other manually operable controls. An associated cathode ray tube display 552 allows the operator to observe the reconstructed image and other data from the computer 546. The operator supplied commands are used by the computer 546 under the direction of stored programs to provide control signals and information to the DAS 544, the x-ray controller 542 and the motor controllers 547 and 548. In addition, computer 46 operates a table motor controller 554 which controls the motorized table 516 to position the patient with respect to the system isocenter 536.

The computer 546 stores programs which enable it to perform a scan in which physiological information can be extracted to indicate the perfusion of blood into tissues. A first reference image is acquired prior to contrast injection using a tomosynthesis method and then a series of tomosynthesis images are acquired at one second intervals as the contrast agent flows into the region of interest. After subtraction of the reference image, these tomosynthesis images are used to calculate regional blood flow (rBF), regional blood volume (rBV) and regional mean transit time (rMTT) and produce corresponding parametric images.

Figure 23:
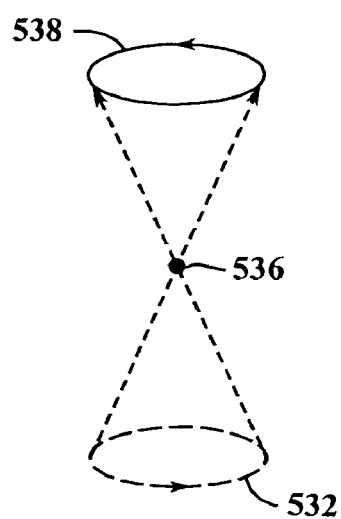
FIG. 23 is a pictorial view of the tomosynthesis scan path used in the method of FIG. 22.
Figure 22:
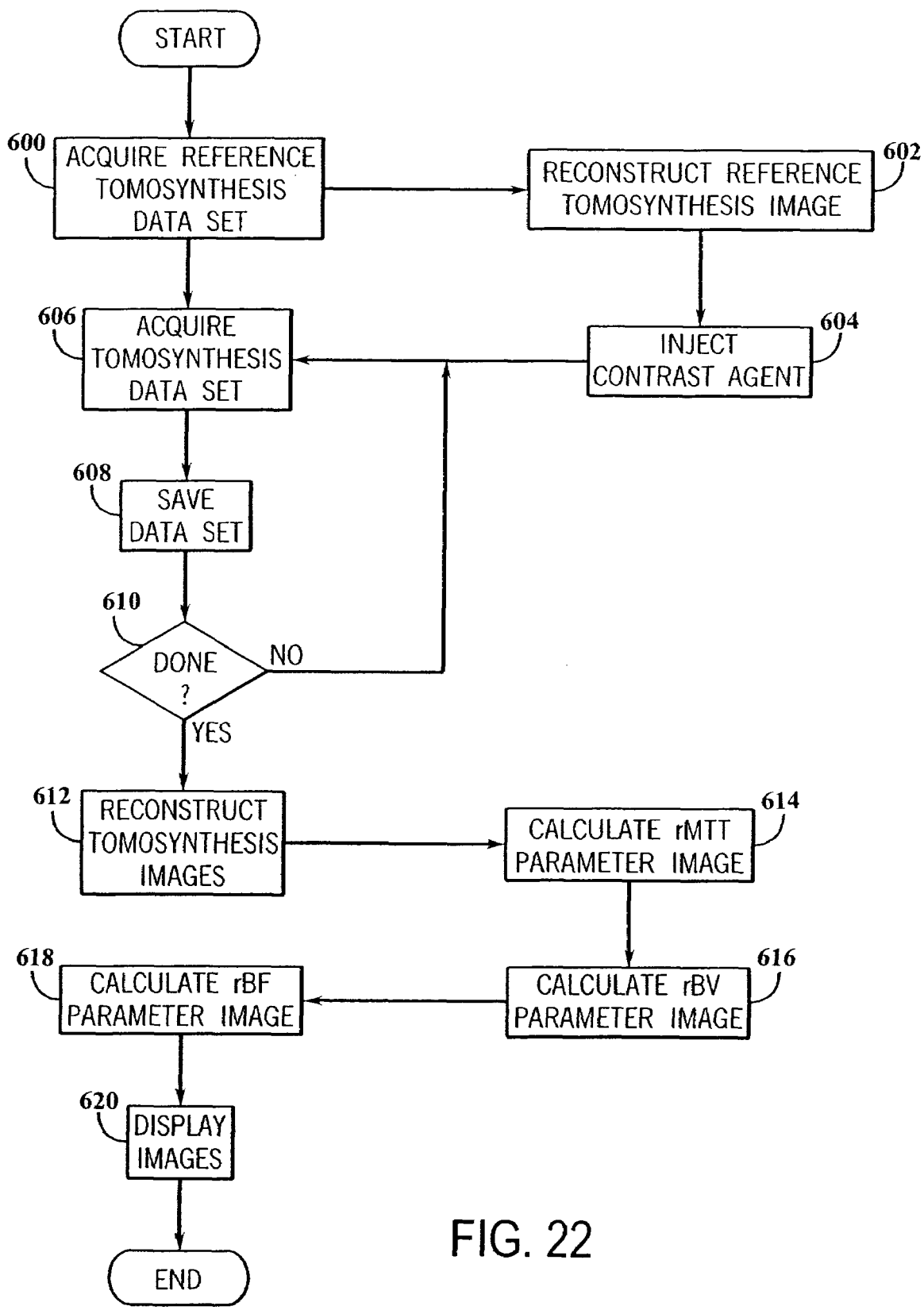
FIG. 22 is a flow chart of another embodiment of the invention in a tomosynthesis scan performed by the system of FIG. 19.

Referring particularly to FIG. 22, when the scan is performed the gantry is moved in a prescribed path to acquire a reference tomosynthesis data set as indicated at process block 600. As shown in FIG. 23, this scan path is performed by simultaneously operating the pivot axis motor controller 547 and C-axis motor controller 548 to move the x-ray source 532 in a circular or elliptical orbit below the isocenter 536 and the detector 538 in a corresponding circular orbit above the isocenter 536. The size of the circular orbit is determined by a number of factors, but the objective is to make the enclosed area of the path as large as possible. The constraining factor is that the gantry should move through the entire circular path to acquire a single tomosynthesis data set at the frame rate needed to capture the dynamic changes that occur during the inflow of contrast agent. In this embodiment of the invention up to 10 tomosynthesis image data sets are acquired in this manner and corresponding views are averaged to form the reference tomosynthesis data set.

As indicated at process block 602, a reference tomosynthesis image is reconstructed from the acquired reference data set. Each acquired view in the reference data set is a radiograph acquired at a specific point on the circular scan path. A 2D image is reconstructed by superimposing these radiograph views and translating them with respect to each other. The location of the 2D image plane is determined by the degree of translation and the 2D tomogram can thus be selectively located above or below the system isocenter 536.

As indicated at process block 604, after acquisition of the reference tomosynthesis image the subject is injected with a contrast agent and a loop is entered in which a series of tomosynthesis data sets are acquired as the contrast flows into the region of interest. The x-ray source 532 and detector array 538 are continuously moved in the circular paths as shown in FIG. 23 and views are continuously acquired as indicated at process block 606. At the completion of each circular scan (approximately one second) the acquired views are saved as a tomosynthesis data set as indicated at process block 608. This data acquisition continues long enough to capture the entire tissue contrast enhancement curve, which can range from approximately 15 seconds to 60 seconds, depending on the location and rate of the injection, the region of interest and the type of pathological conditions present. The data acquisition phase is then complete as indicated at decision block 610, and each of the acquired tomosynthesis data sets are used to reconstruct corresponding image frames as indicated at process block 612. The reconstruction of the tomosynthesis image frames according to the present invention is described in more detail below After each image frame is reconstructed the reference tomosynthesis image is subtracted from it. The result is a series of difference tomosynthesis images which depict the inflow of blood into the arteries and tissues in the region of interest. This information is used to calculate a number of parameters which measure the blood perfusion in the tissues. Usually, the tomosynthesis images will be reconstructed at more than one plane so that blood perfusion can be assessed at different locations in the region of interest. Also, to make the parameter calculations an arterial contrast enhancement curve is needed and this requires tomosynthesis images in a plane that contains the artery that supplies blood to the tissues of interest.

As indicated at process block 614, an image which depicts the regional mean transit time (rMTT) of blood flow into tissues is calculated by deconvolving tissue contrast enhancement curves and the arterial contrast enhance curve. Both curves are obtained from the set, or sets, of tomosynthesis images. As indicated at process block 616, a regional blood flow volume (rBV) image is then calculated. The volume of flowing blood in a capillary network is calculated by the ratio of two areas under the tissue enhancement curve and arterial enhancement curve. And finally, a regional blood flow (rBF) image is calculated at process block 618. The blood flow information is derived from the rBV and rMTT information using the central volume principle.

Figure 24:
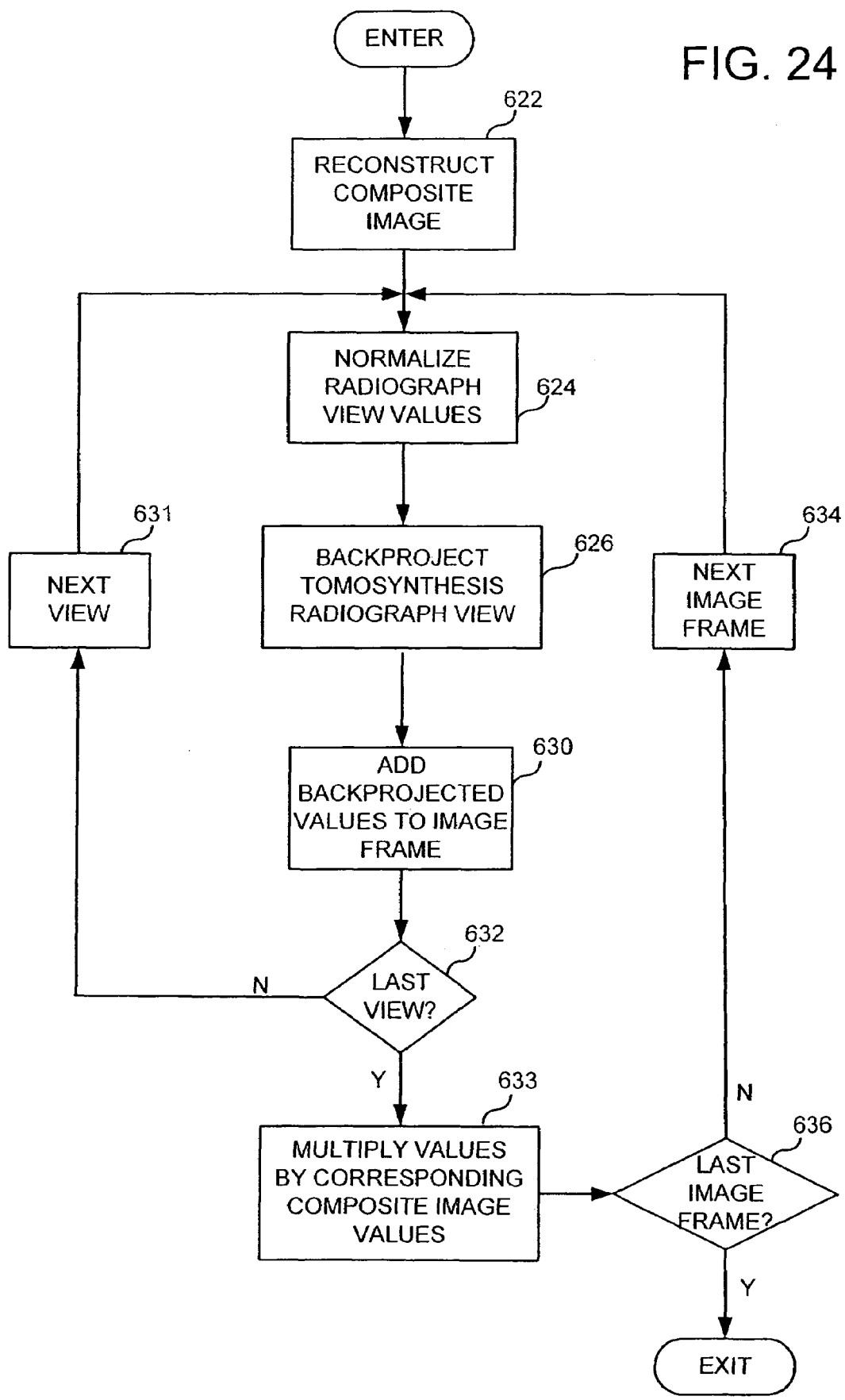
FIG. 24 is a flow chart of the image frame reconstruction method of the present invention used in the tomosynthesis scan of FIG. 22.

Referring particularly to FIG. 24, the reconstruction of the tomosynthesis image frames is performed by constraining the reconstruction with a composite image. The first step, therefore, is to produce the composite image as indicated at process block 622. This is done by combining the corresponding radiograph views in the respective tomosynthesis data sets to produce a composite tomosynthesis data set. More specifically, corresponding values (i.e., same radiograph view angle and x,y location therein) in the tomosynthesis data sets are averaged to produce the composite tomosynthesis data set. A tomosynthesis reconstruction algorithm is then used to produce one or more composite image slices from this composite tomosynthesis data set. A number of standard methods may be used for this step such as that disclosed in U.S. Pat. No. 4,903,204.

A loop is then entered in which an image frame is reconstructed from each acquired tomosynthesis data set. First, one view in the data set is normalized as indicated at process block 624. This is accomplished by dividing each value therein by the corresponding projection value in the same view of the composite tomosynthesis data set. The normalized values in the radiograph view are then backprojected as indicated at process block 626. This is an unconstrained backprojection which uses the same algorithm used to produce the composite image. As indicated by process block 630, the resulting values are added to the image frame being reconstructed.

This process repeats for each view in the acquired tomosynthesis data set as indicated at block 631 until all views in the current image frame have been processed as determined at decision block 632. The resulting slice image(s) is then constrained as indicated at process block 633 by multiplying each pixel value therein by the corresponding pixel value in the composite image. The process is then repeated for each image frame as indicated at process block 634 until all the tomosynthesis data sets have been processed to produce corresponding image frames as determined at decision block 636.

There are many variations possible from the particular embodiments described above. For example, the multiplication by the composite image in Radon space or real space can also be equivalently performed in k-space. Similarly, the normalization step performed in Radon space in the above-described embodiments can also be equivalently performed in k-space. Also, it is possible to use the present invention to improve the quality of existing images. In a PET scan, for example, there is usually complete sampling and the issue is noise. The fully sampled image can be reprojected and the resulting projections may be used in a highly constrained backprojection according to the present invention to reconstruct images with a higher SNR.

The present invention is particularly applicable to clinical applications in which the clinically important structures are not accompanied by substantial background structures. Such "sparse" images enable a nearly exact image reconstruction to be performed because the backprojected signals are focused on the target structures rather than being disbursed to background structures. Such sparsity is enhanced in the above-described CEMRA clinical applications by subtracting out non-vasculature structure with a mask image prior to image reconstruction. It is contemplated that the present invention may be successfully applied to other clinical applications where considerable background structures are present by subtracting similar image data prior to image reconstruction to form a sparse data set, and then adding it back after image reconstruction.

In the preferred MRI embodiments of the invention radial k-space projection views are acquired and these are Fourier transformed to Radon space for image reconstruction according to the present invention. Other k-space sampling trajectories may also be used. One variation is to acquire a partial NMR echo signal which samples along a trajectory that does not extend across the entire extent of the sampled k-space volume. Another variation which is equivalent to the straight line projection reconstruction pulse sequence is to sample along a curved path rather than a straight line. Such pulse sequences are described, for example, in "Fast Three Dimensional Sodium Imaging", MRM, 37:706-715, 1997 by F. E. Boada, et al. and in "Rapid 3D PC-MRA Using Spiral Projection Imaging", Proc. Intl. Soc. Magn. Reson. Med. 13 (2005) by K. V. Koladia et al and "Spiral Projection Imaging: a new fast 3D trajectory", Proc. Intl. Soc. Mag. Reson. Med. 13 (2005) by J. G. Pipe and Koladia. Regardless of the sampling trajectory used, the k-space sample points can be regridded to form a set of radial projections that can be processed according to the teachings of the present invention.

What is claimed is:

1. A method for producing an image of a subject positioned in a field of view (FOV) of an imaging system, the steps comprising:
   a) acquiring with the imaging system a plurality of views of the subject positioned in the FOV;
   b) producing an image data set from views acquired in step a);
   c) producing a composite image by combining views acquired in step a), wherein the views combined to produce the composite image includes the views used to produce the image data set and additional acquired views; and
   d) reconstructing an image of the subject by normalizing the image data set with information derived from the composite image and by multiplying the normalized result with the composite image.

2. The method as recited in claim 1 in which the imaging system is a medical imaging system, the views acquired in step a) are projection views and step d) includes:
   d)i) backprojecting projection views into the FOV and weighting the value backprojected into each image pixel by the composite image; and
   d)ii) summing the backprojected values for each image pixel.

3. The method as recited in claim 2 in which each image pixel backprojected value $S_n$ is calculated in step d)i) as $$S_n = (P \times C_n) \Big/ \sum_{n=1}^{N} C_n$$

where: P=the projection view value being backprojected;
   $C_n$=corresponding pixel value in the composite image;
   $S_n$=the value of the $n^{th}$ pixel along the backprojection path; and
   N=total number of pixels along the backprojection path.

4. The method as recited in claim 2 in which step c) includes editing the composite image to remove an object therein and to thereby substantially minimize the appearance of that object in the reconstructed image.

5. The method as recited in claim 2 in which the weighting in step d)i) includes normalizing each projection view using a corresponding projection view from the composite image and multiplying the backprojected value by the value of the corresponding pixel in the composite image.

6. The method as recited in claim 5 in which the composite image is produced using substantially all the projection views acquired in step a).

7. The method as recited in claim 2 in which the FOV is three-dimensional, a three-dimensional image is produced, and the image $I_{(x,y,z)}$ reconstructed in step c) is:

$$I(x, y, z) = \sum (P(r, \theta, \phi) * C(x, y, z)_{(r,\theta,\phi)} / P_c(r, \theta, \phi))$$

where the summation ($\Sigma$) is over all projection views used to reconstruct the image; $I_{(x,y,z)}$ is the image value at pixel location x,y,z; $P_{(r,\theta,\phi)}$ is the back projected value from the projection view at view angle $\theta$, $\phi$; $C_{(x,y,z)}$ is the composite image value at the pixel location x,y,z; and $P_c(r,\theta,\phi)$ is the projection profile value from the composite image at the view angle $\theta$, $\phi$.

8. The method as recited in claim 2 in which the projection views are acquired in step a) by accumulating counts over a period of time, the projection views used in step c) to produce the composite image include counts accumulated over substantially the entire period of time, and the projection views used in step b) include counts accumulated over a portion of said period of time.

9. The method as recited in claim 8 in which the medical imaging system is a PET scanner and the counts represent the number of detected positron electron annihilation events.

10. The method as recited in claim 8 in which the medical imaging system is a SPECT scanner and the courts represent the number of detected photons.

11. The method as recited in claim 3 which includes:
   e) acquiring with the medical imaging system additional views of the subject positioned in the FOV;
   f) reconstructing a mask image from the additional views; and
   g) subtracting the mask image from the composite image prior to performing step d).

12. The method as recited in claim 1 in which the views acquired in step a) are radiograph views repeatedly acquired at the same view angle.

13. The method as recited in claim 11 in which the composite image is reconstructed using a tomosynthesis reconstruction.

14. The method as recited in claim 1 in which the imaging system is a medical imaging system, and step d) includes:
   d)i) producing a constrained image of the subject in the FOV by multiplying values in the image data set at each image pixel location by the corresponding pixel value in the composite image; and
   d)ii) producing the image of the subject by normalizing the constrained image.

15. The method as recited in claim 14 in which the image data set is formed from views acquired in step a) that depict the subject in the FOV from a set of projection angles and the constrained image is normalized in step d)ii) by:
   calculating a projection of the composite image at each of the projection angles; and
   dividing each pixel value in the constrained image by a value in each of the composite image projections.

16. The method as recited in claim 15 in which the views acquired in step a) are projection views acquired at interleaved projection angles, the image data set produced in step b) includes producing the image data set from a set of said projection views, and the constrained image is normalized in step d)ii) by:
   calculating a projection of the composite image at each projection angle of the set of said projection views; and
   dividing each pixel value in the constrained image by a value in each of the composite image projections.

17. The method as recited in claim 14 in which the image data set produced in step b) includes:
   selecting a set of views acquired in step a); and
   transforming the selected views from acquisition space to real space.

18. The method as recited in claim 17 in which acquisition space is k-space and the transformation is an inverse Fourier transformation.

19. The method as recited in claim 18 in which the selected views are projection views and the transformation includes transforming the projection views to k-space.

20. The method as recited in claim 17 in which acquisition space is Radon space and the transformation is a backprojection of each view.

21. The method as recited in claim 15 in which the composite image is reconstructed from substantially all the views acquired in step a); and the image data set is produced in step b) from substantially less than all the views acquired in step a).

22. The method as recited in claim 14 which includes:
   d) producing additional images of the subject by repeating steps b) and d) using different ones of the views acquired in step a).

23. The method as recited in claim 22 in which the views acquired in step a) are projection views acquired at different view angles.

24. The method as recited in claim 14 in which the views acquired in step a) are acquired over a period of time during which changes occur in the subject; step b) includes selecting a set of views acquired during a time interval during the performance of step a); and step c) includes selecting a set of views acquired during a window of time that includes said time interval and is longer than said time interval.

25. The method as recited in claim 14 in which the medical imaging system is a magnetic resonance imaging system and each view samples a line in k-space.

26. The method as recited in claim 14 in which the medical imaging system is an x-ray CT system and each view is a projection in Radon space.

27. The method as recited in claim 14 in which the medical imaging system is an x-ray system and each view is a radiograph.

28. The method as recited in claim 1 in which the composite image provides a priori knowledge of the subject to be imaged; and
   wherein the a priori knowledge of the subject in the composite image is used in the image reconstruction to improve the quality of the image.

29. The method as recited in claim 28 in which step d) includes:
   d)i) backprojecting a selected view into the FOV; and
   d)ii) weighting the value backprojected into each FOV image pixel based on the a priori knowledge of the subject at the image pixel.

30. The method as recited in claim 29 in which step d)ii) includes:
   multiplying each backprojected image pixel value by a value in the composite image; and
   normalizing the product of said multiplication.

31. The method as recited in claim 29 in which step d) includes Fourier transforming each selected view prior to backprojection in step d)i).

32. The method as recited in claim 28 in which step d) includes:
   d)i) transforming the image data set to a real space image; and d)ii) weighting the values of the real space image pixels based on the a priori knowledge of the subject at each image pixel.

33. The method as recited in claim 32 in which the transformation in step d)i) is an inverse Fourier transformation.

34. The method as recited in claim 1 in which the imaging system is a medical imaging system, and step d) includes:
d)i) normalizing the image data set by dividing values therein by values derived from the composite image;
d)ii) transforming the normalized image data set to form an unconstrained image; and
d)iii) multiplying values in the unconstrained image by corresponding values in the composite image.

35. The method as recited in claim 34 in which the values used in step d)i) are derived from the composite image by calculating a projection of the composite image for each view in the image data set.

36. The method as recited in claim 34 in which the views acquired in step a) are projection views acquired at interleaved projection angles, the image data set produced in step b) includes producing the image data set from a set of said projection views, and the image data set is normalized in step d)i) by:
calculating a projection of the composite image at each projection angle of the set of said projection views; and
dividing each value in the image data set by a value in each of the composite image projections.

37. The method as recited in claim 34 in which the composite image is reconstructed from substantially all the views acquired in step a); and the image data set is produced in step b) from substantially less than all the views acquired in step a).

38. The method as recited in claim 35 which includes:
e) producing additional images of the subject by repeating steps b) and d) using different ones of the views acquired in step a).

39. The method as recited in claim 34 in which the views acquired in step a) are acquired over a period of time during which changes occur in the subject; step b) includes selecting a set of views acquired during a time interval during the performance of step a); and step c) includes selecting a set of views acquired during a window of time that includes said time interval and is longer than said time interval.

40. The method as recited in claim 34 in which the transformation in step d)ii) is a Fourier transformation.

41. The method as recited in claim 34 in which the transformation in step d)ii) includes:
Fourier transforming each normalized image data set view; and
reconstructing the unconstrained image from the Fourier transformed image data set views by performing one of either a two-dimensional or a three-dimensional inverse Fourier transformation thereon.

42. The method as recited in claim 35 in which step c) includes editing the composite image to remove selected structures.

43. The method as recited in claim 42 which includes reconstructing a mask image from selected views acquired in step a) and the editing of the composite image includes subtracting the mask image.

* * * * *

UNITED STATES PATENT AND TRADEMARK OFFICE
CERTIFICATE OF CORRECTION

| | | |
|---|---|---|
| PATENT NO. | : 7,519,412 B2 | Page 1 of 1 |
| APPLICATION NO. | : 11/482372 | |
| DATED | : April 14, 2009 | |
| INVENTOR(S) | : Charles A. Mistretta | |

It is certified that error appears in the above-identified patent and that said Letters Patent is hereby corrected as shown below:

Column 23, claim 10, line 24, "courts" should be --counts--.

Signed and Sealed this

Twenty-sixth Day of May, 2009

JOHN DOLL
*Acting Director of the United States Patent and Trademark Office*